United States Patent
Ping et al.

(10) Patent No.: US 7,322,066 B2
(45) Date of Patent: Jan. 29, 2008

(54) ELECTRIC TOOTHBRUSHES HAVING MOVABLE, INTERMITTENTLY MOVABLE, AND FIXED BRISTLES

(75) Inventors: Wang Ping, Beijing (CN); John Geoffrey Chan, Loveland, OH (US)

(73) Assignee: Church & Dwight Co., Inc., Princeton, NJ (US)

( * ) Notice: Subject to any disclaimer, the term of this patent is extended or adjusted under 35 U.S.C. 154(b) by 658 days.

(21) Appl. No.: 10/780,365

(22) Filed: Feb. 17, 2004

(65) Prior Publication Data

US 2005/0011024 A1 Jan. 20, 2005

Related U.S. Application Data

(60) Provisional application No. 60/487,670, filed on Jul. 16, 2003.

(51) Int. Cl.
*A46B 13/00* (2006.01)

(52) U.S. Cl. ............................ 15/22.1; 15/28

(58) Field of Classification Search ............ None
See application file for complete search history.

(56) References Cited

U.S. PATENT DOCUMENTS

| | | |
|---|---|---|
| 3,524,088 A | 8/1970 | Ryckman, Jr. |
| 4,156,620 A | 5/1979 | Clemens |
| 4,827,550 A | 5/1989 | Graham et al. |
| 4,845,795 A | 7/1989 | Crawford et al. |
| 4,989,287 A | 2/1991 | Scherer |
| 5,033,150 A | 7/1991 | Gross et al. |
| 5,226,206 A | 7/1993 | Davidovitz |
| 5,253,382 A | 10/1993 | Beny |
| 5,353,460 A | 10/1994 | Bauman |
| 5,359,747 A | 11/1994 | Amakasu |
| 5,448,792 A | 9/1995 | Wiedemann |
| 5,504,959 A | 4/1996 | Yukawa et al. |
| 5,617,601 A | 4/1997 | McDougall |
| 5,836,030 A | 11/1998 | Hazeu et al. |
| 5,842,245 A | 12/1998 | Pai |
| 5,876,206 A | 3/1999 | Mauer |
| 6,000,083 A | 12/1999 | Blaustein et al. |
| D432,312 S | 10/2000 | Blaustein et al. |
| D433,814 S | 11/2000 | Blaustein et al. |

(Continued)

FOREIGN PATENT DOCUMENTS

CA 972244 8/1975

(Continued)

*Primary Examiner*—David Redding
(74) *Attorney, Agent, or Firm*—K. Bradford Adolphson

(57) ABSTRACT

An electric toothbrush comprising a handle, a head, and a neck extending between the handle and the head. The electric toothbrush has a longitudinal axis. The handle has a hollow interior region, and has a motor disposed within the hollow region. The movable bristle holder is disposed on the head, and has a plurality of movable bristles disposed thereon. The drive shaft operatively connects the motor to the movable bristle holder to move the movable bristle holder and the bristles disposed on the movable bristle holder. The head has bristles disposed thereon. One or more bristles are disposed on a static portion of the head of the toothbrush. Movement of the drive shaft and/or the movable bristle holder results in movement of at least a portion of the one or more bristles disposed on the static portion of the toothbrush head.

54 Claims, 13 Drawing Sheets

U.S. PATENT DOCUMENTS

| | | |
|---|---|---|
| 6,178,579 B1 | 1/2001 | Blaustein et al. |
| 6,189,693 B1 | 2/2001 | Blaustein et al. |
| 6,237,178 B1 | 5/2001 | Krammer et al. |
| 6,311,837 B1 | 11/2001 | Blaustein et al. |
| 6,314,605 B1 | 11/2001 | Solanki et al. |
| 6,360,395 B2 | 3/2002 | Blaustein et al. |
| 6,371,294 B1 | 4/2002 | Blaustein et al. |
| D456,998 S | 5/2002 | Blaustein et al. |
| D457,728 S | 5/2002 | Blaustein et al. |
| D458,030 S | 6/2002 | Blaustein et al. |
| D458,455 S | 6/2002 | Blaustein et al. |
| D459,584 S | 7/2002 | Blaustein et al. |
| D459,895 S | 7/2002 | Blaustein et al. |
| D461,642 S | 8/2002 | Blaustein et al. |
| D461,959 S | 8/2002 | Chan et al. |
| D459,894 S | 9/2002 | Blaustein et al. |
| D465,088 S | 11/2002 | Blaustein et al. |
| 6,546,585 B1 | 4/2003 | Blaustein et al. |
| 6,564,940 B2 | 5/2003 | Blaustein et al. |
| 6,581,233 B1 | 6/2003 | Cheng et al. |
| D476,486 S | 7/2003 | Blaustein et al. |
| D483,182 S | 12/2003 | Blaustein et al. |
| 6,813,793 B2 * | 11/2004 | Eliav .................. 15/22.2 |
| 2001/0022277 A1 | 9/2001 | Blaustein et al. |
| 2002/0020645 A1 | 2/2002 | Blaustein et al. |
| 2002/0029988 A1 | 3/2002 | Blaustein et al. |
| 2002/0032941 A1 | 3/2002 | Blaustein et al. |
| 2002/0078514 A1 | 6/2002 | Blaustein et al. |
| 2002/0162180 A1 | 11/2002 | Blaustein et al. |
| 2003/0084528 A1 | 5/2003 | Blaustein et al. |
| 2003/0126698 A1 | 7/2003 | Fritsch et al. |
| 2003/0140435 A1 | 7/2003 | Eliav |
| 2003/0163882 A1 | 9/2003 | Blaustein et al. |
| 2003/0166373 A1 | 9/2003 | Blaustein et al. |
| 2003/0221267 A1 | 12/2003 | Chan |
| 2003/0226223 A1 | 12/2003 | Chan |
| 2004/0060133 A1 | 4/2004 | Eliav |
| 2004/0107521 A1 | 6/2004 | Chan et al. |
| 2004/0128780 A1 | 7/2004 | Chan |
| 2004/0134001 A1 | 7/2004 | Chan |
| 2004/0177458 A1 | 9/2004 | Chan et al. |
| 2004/0200016 A1 | 10/2004 | Chan et al. |

FOREIGN PATENT DOCUMENTS

| | | |
|---|---|---|
| CA | 1082408 | 7/1980 |
| CA | 1191003 | 7/1985 |
| CA | 96826 | 7/2002 |
| CN | 2274947 | 2/1998 |
| DE | 1244709 | 7/1967 |
| DE | 29517610 | 4/1997 |
| EP | 054043 | 11/1985 |
| EP | 651978 | 10/1995 |
| FR | 1357566 | 4/1964 |
| FR | 1357570 | 4/1964 |
| FR | 1414679 | 9/1965 |
| FR | 2368854 | 5/1978 |
| GB | 2005999 | 5/1979 |
| GB | 2089042 | 3/2001 |
| GB | 2094145 | 3/2001 |
| GB | 2097844 | 3/2001 |
| GB | 2097845 | 3/2001 |
| GB | 3008453 | 5/2003 |
| GB | 3004567 | 9/2003 |
| GB | 3004568 | 9/2003 |
| GB | 3014059 | 9/2003 |
| GB | 3014060 | 9/2003 |
| GB | 3006685 | 10/2003 |
| GB | 3006686 | 10/2003 |
| JP | 5-146313 | 6/1993 |
| JP | 5-146314 | 6/1993 |
| JP | 5-199917 | 8/1993 |
| JP | 5-269024 | 10/1993 |
| JP | 6-121710 | 5/1994 |
| JP | 6-189822 | 7/1994 |
| JP | 6-245819 | 9/1994 |
| JP | 6-245820 | 9/1994 |
| JP | 7-116020 | 5/1995 |
| JP | 7-116024 | 5/1995 |
| JP | 7-93892 | 10/1995 |
| JP | 8-000356 | 1/1996 |
| JP | 8-103331 | 4/1996 |
| JP | 2540444 | 4/1997 |
| JP | 2719556 | 11/1997 |
| JP | 2804940 | 7/1998 |
| JP | 2811246 | 8/1998 |
| JP | 3005608 | 11/1999 |
| JP | 3045412 | 3/2000 |
| JP | 1149999D | 6/2002 |
| JP | 1189181 | 9/2003 |
| KR | 1997-0000408 | 1/1997 |
| KR | 1997-0000409 | 1/1997 |
| KR | 125188 | 10/1997 |
| TW | 212909 | 9/1993 |
| WO | WO 91/13570 | 9/1991 |
| WO | WO 96/09019 | 3/1996 |
| WO | WO 96/10373 | 4/1996 |
| WO | WO 96/38100 | 12/1996 |
| WO | WO 02/089929 | 11/2002 |
| WO | WO 03/039396 A1 | 5/2003 |
| WO | WO 03/043459 A2 | 5/2003 |
| WO | WO 03/082049 A | 10/2003 |
| WO | WO 03/082050 A1 | 10/2003 |
| WO | WO 03/103531 A1 | 12/2003 |
| WO | WO 2004/093719 | 11/2004 |

* cited by examiner

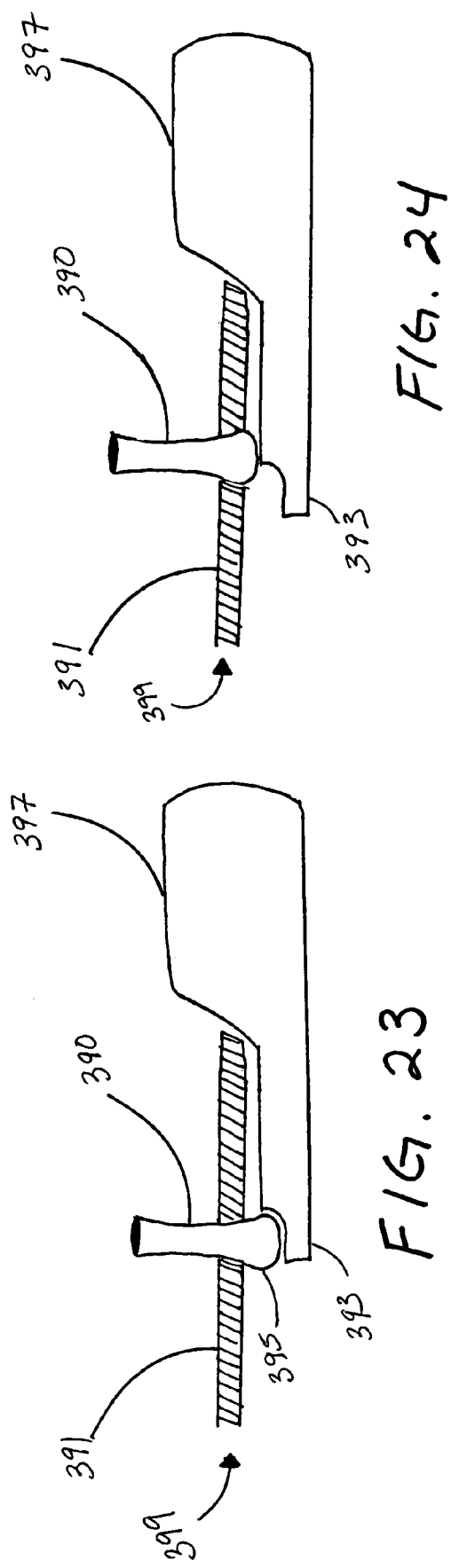

ELECTRIC TOOTHBRUSHES HAVING MOVABLE, INTERMITTENTLY MOVABLE, AND FIXED BRISTLES

CROSS REFERENCE TO RELATED APPLICATION

This application claims priority from U.S. provisional application Ser. No. 60/487,670 filed Jul. 16, 2003 which is herein incorporated by reference.

FIELD OF THE INVENTION

The present invention relates to the field of toothbrushes, and more particularly, the invention relates to the field of electrically powered toothbrushes.

BACKGROUND OF THE INVENTION

Toothbrushes have traditionally utilized one or more groups of bristles that are fixed or otherwise attached to the head or end of the toothbrush. Toothbrushes are also known that utilize movable bristles that are mechanically or electrically powered. Typically, an electric motor and a drive mechanism are retained within the body of the toothbrush and are coupled to the movable bristles. Upon actuation of the motor and drive mechanism, the bristles may undergo a variety of different types of motion.

Each type of toothbrush offers certain advantages and exhibits particular characteristics, some of which the other type do not provide. Accordingly, it would be desirable to combine features and aspects of fixed bristles with those of movable or powered bristles.

Although toothbrushes are known in the prior art that utilize movable or powered bristles in combination with fixed bristles, it is believed that further improvements in cleaning efficacy and manufacturability are still attainable. Accordingly, there is a need for a toothbrush having one or more fixed bristle(s) in conjunction with one or more movable and/or powered bristle(s) that provides robust cleaning efficacy and which is economical and well suited for large scale manufacturing.

SUMMARY OF THE INVENTION

An electric toothbrush comprising a handle, a head, and a neck extending between the handle and the head. The handle has a hollow interior region, and has a motor disposed within the hollow region. A movable bristle holder can be disposed on the head, and can have a plurality of movable bristles disposed thereon. The motor can be operatively connected to the movable bristle holder by the drive shaft. One or more bristles can be disposed on a static portion of the head. Movement of the drive shaft and/or the movable bristle holder can result in movement of at least a portion of one or more of the bristles disposed on the static portion of the head of the toothbrush.

BRIEF DESCRIPTION OF THE DRAWINGS

The present invention may take form in various components and arrangements of components, and in various techniques, methods, or procedures and arrangements of steps. The referenced drawings are only for purposes of illustrating preferred embodiments, they are not necessarily to scale, and are not to be construed as limiting the present invention.

It is believed that the present invention will be better understood from the following description taken in conjunction with the accompanying drawings in which:

FIG. 23 is a detailed cut away view of the head portion of the toothbrush illustrating the movement of the bristle holder along the head portion.

FIG. 24 is a detailed cut away view of the head portion of the toothbrush illustrating further movement of the bristle holder along the head portion.

DETAILED DESCRIPTION OF THE PREFERRED EMBODIMENTS

Figure 1:
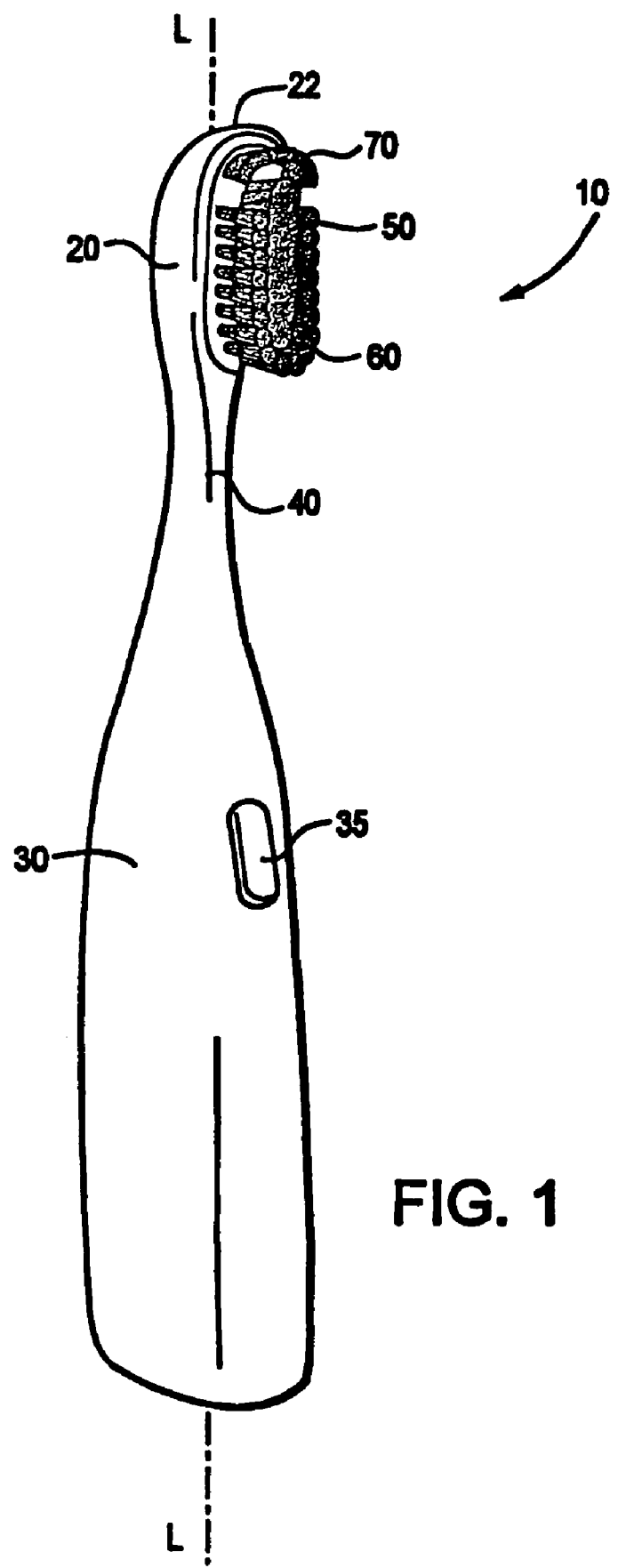
FIG. 1 is a perspective view of a preferred embodiment toothbrush in accordance with the present invention.

The present invention is based upon a discovery that significant cleaning efficacy results from a toothbrush that utilizes a combination of fixed bristles, movable bristles, and intermittently movable bristles. This toothbrush can be used to clean any teeth including natural and/or replacement teeth. Additionally, this toothbrush can be used in any oral cavity including the mouths of humans and/or animals. The present invention is additionally based upon a discovery of a unique configuration between the intermittently movable bristles and the drive shaft and/or the movable bristle holder. Bristles disposed in static portions of the head can undergo movement as a result of movement of the drive shaft and/or the movable bristle holder of the toothbrush. The present invention is also based upon a discovery of particular patterns or configurations of one or more fixed bristles, particularly when utilized in conjunction with the movable and powered bristle set and the intermittently movable bristles. Furthermore, the present inventive toothbrush, featuring a moveable bristle holder that reciprocates and which is at least partially surrounded by an array of fixed bristles, is particularly well suited for large scale manufacturing. That is, the various preferred embodiment brushes described herein are relatively inexpensive to manufacture as a result of their remarkable simplicity and novel structure. These and other aspects are described herein.

Conventionally bristles are generally cylindrical, elongate, and extend upward from the bristle bearing surface of the head of the toothbrush. These bristles typically comprise nylon and can be disposed on the head of the toothbrush in tufts, and/or groups of bristles. The term bristles as used herein is intended to be used in a generic sense as cleaning and/or massaging elements and includes, but is not limited to, conventional bristles, elastomeric bristles, elastomeric fingers, and/or elastomeric walls. Examples of elastomeric bristles, fingers and walls suitable for use with the present invention are described in U.S. Pat. Nos. 5,628,082, 5,335,389, and U.K. Patent Application No. G.B. 2,371,217, and U.S. Application Nos. 2003/0196283, 2003/0033682 and 2003/0033680, and are all incorporated by reference herein.

Before describing the various preferred embodiments, it is instructive to define the various types of motions that the movable bristles and movable bristle holder may undergo. As used herein, the term "angular motion" refers to any angular displacement. "Linear motion" is movement along a straight or substantially straight, line or direction. "Primarily linear motion" is described below. "Curvilinear motion" is movement that is neither completely linear nor completely angular but is a combination of the two (e.g., curvilinear). These motions can be constant or periodic. Constant motion refers to motion that does not change direction or path (i.e., is unidirectional). Periodic motion refers to motion that reverses direction or path. Constant angular motion (i.e., motion that extends through 360 degrees or more) that is substantially in the form of a circle is referred to as rotary motion. Periodic angular motion is motion that extends through less than 360 degrees and is referred to as oscillating motion. Curvilinear motions can also be either constant (i.e., unidirectional) or periodic (i.e., reverses direction). Periodic linear motion is referred to as "reciprocation". The above-described motions can also occur along one or more axes of a bristle holder.

Furthermore, it is useful to define the terms "fixed bristles," "movable bristles." and "intermittingly movable bristles." The term "fixed bristles" refers to bristles that are secured or affixed to the brush head or body of the toothbrush or other component thereof so that the bristles, and specifically, the base of the bristles, do not move with regard to the longitudinal axis of the toothbrush. Restated, fixed bristles refer to bristles that are affixed to the toothbrush such that their base or point of attachment does not move with respect to the toothbrush and the base and/or the regions of the bristle distal from the base do not move with respect to the brush as a result of movement of the drive shaft or movable bristle holder of the inventive toothbrush. It is recognized that the tips or regions distal from the base of a bristle or group of bristles may move as a result of flexing not resulting from movement of the drive shaft and/or movable bristle holder.

The term "movable bristle" refers to bristles disposed on a bristle holder that is driven by the motor to move with respect to the toothbrush, preferably along the longitudinal axis of the brush. Movable bristles are powered, as they are disposed on and supported by a movable bristle holder. Preferably, the movable bristles reciprocate when powered, and most preferably, the movable bristles reciprocate in a direction generally parallel to the longitudinal axis of the toothbrush. It is contemplated that the movable bristles may also reciprocate in a direction generally perpendicular to the longitudinal axis. Although reciprocation is the preferred type of movement for the movable bristle holder, the present invention encompasses any and all other types of movement for the movable bristle holder.

The term "intermittently movable" bristle refers to bristles that are disposed in, on and/or passes through a static portion of the head of the toothbrush and which undergo motion as a result of movement of the drive shaft and/or the movable bristle holder of the toothbrush of the present invention. A portion of the head is static if the portion does not move, and in particular the portion does not result in movement via an operative connection to the drive shaft and/or motor of the toothbrush. In one embodiment the bristles disposed on the static portion of the head of the toothbrush move as a result of contact between these bristles and the movable bristle holder. The movable bristle holder moves as a result of an operative connection with the drive shaft of the toothbrush. In another embodiment, movement of the drive shaft results in movement of another element disposed on the head of the toothbrush which contacts at least a portion of the one or more intermittently movable bristle(s), thereby resulting in movement of at least a portion of one or more of the intermittently movable bristle(s). In yet another embodiment the drive shaft itself contacts one or more of the intermittently movable bristle(s), resulting in movement of at least a portion of one or more of the intermittently movable bristle(s).

As described herein intermittently movable bristles undergo motion as a result of application of a force generally applied in a direction transverse to the orientation of the bristles that causes displacement of the bristles. The amplitude and frequency of displacement of the intermittently movable bristle can be dependent on the movement of the movable bristle holder and/or drive shaft, and the type and/or location of contact between the movable bristle holder and/or drive shaft and the intermittently movable bristle(s). The bristle can be impacted anywhere on the length or perimeter, including but not limited to, the top, side, leading edge, trailing edge, bristle bulb and/or base and/or any combination thereof. A bristle bulb and/or base comprises the terminal end of the bristle typically inside the head of the toothbrush. The bristle bulb and/or base is the fused terminal ends of the bristle tufts. These bristle ends can be fused together by any conventional means including, but not limited to, melting. The resulting motion can include rotation, oscillation, rocking, and moving the intermittently moving bristle up and down and/or side to side, and any combination of these motions. Additionally, the periodic motion or displacement of the intermittently movable bristles can result from impact between the movable bristle holder and/or drive shaft with the bulb or base of the intermittently movable bristle(s). The amplitude of the movement of the intermittently movable bristles can be customized by the type of impact and/or contact of the movable bristle holder and the intermittently movable bristles. For example, the amplitude of the bristle movement can vary depending on which portion or area of the bristle the movable bristle holder and/or drive shaft contacts. Additionally, the amplitude will also vary depending on the stroke length of the movable bristle holder and/or drive shaft, as the stroke length increases, the amplitude can also increase. Generally, the frequency of the movement of the intermittently movable element is dependent upon the frequency of the movement of the movable bristle holder and/or drive shaft.

Often a majority of the length or height of the intermittently movable bristles undergoes some degree of movement or displacement. Furthermore, as described herein, application of the force causing displacement of the intermittently movable bristle is preferably achieved by impacting or contacting the bristles with a component of the toothbrush drive mechanism. A preferred strategy for accomplishing this is to configure a reciprocating bristle holder to strike or contact a group of intermittently movable bristles at one or more locations along the stroke path of the holder. The term intermittently movable bristle also includes bristle configurations in which a moving bristle holder and/or drive shaft periodically contacts or impacts a group or tuft of bristles such that at least a portion, preferably a majority of, and most preferably all of the bristles in the group or tuft undergo intermittent motion. The tufts of bristles may be closely spaced with the other tufts in along the perimeter of the head of the toothbrush thereby giving the appearance of a single unit and/or wall of bristles. However, the tufts may be discretely arranged so as to appear as individual tufts. In this aspect of the invention, a tuft of bristles is disposed in close proximity to a moving bristle holder and/or drive shaft such that upon operation of the toothbrush, the bristle holder, and/or drive shaft periodically contacts or strikes a portion of the bristles located along the periphery or outer region of the tuft. The bristles that are directly contacted by the moving bristle holder and/or drive shaft are intermittently movable bristles. These intermittently movable bristles then contact other bristles within the tuft. The bristles contacted by the intermittently movable bristles are also intermittently movable bristles, as their motion is a result of the contact of the movable bristle carriers and/or drive shaft with bristles disposed in a static portion of the head of the toothbrush. Due to the relative close proximity of the bristles within the tuft, intermittent movement imparted to the bristles along the periphery of the tuft is also imparted to at least some, preferably a majority, and most preferably to all other bristles within the tuft. It is contemplated that such groups or tufts may include elements such as nylon bristles, elastomeric bristles, elastomeric fingers, elastomeric walls and/or any other element that extends upward from the bristle bearing surface of the head of the toothbrush.

Figure 1A:
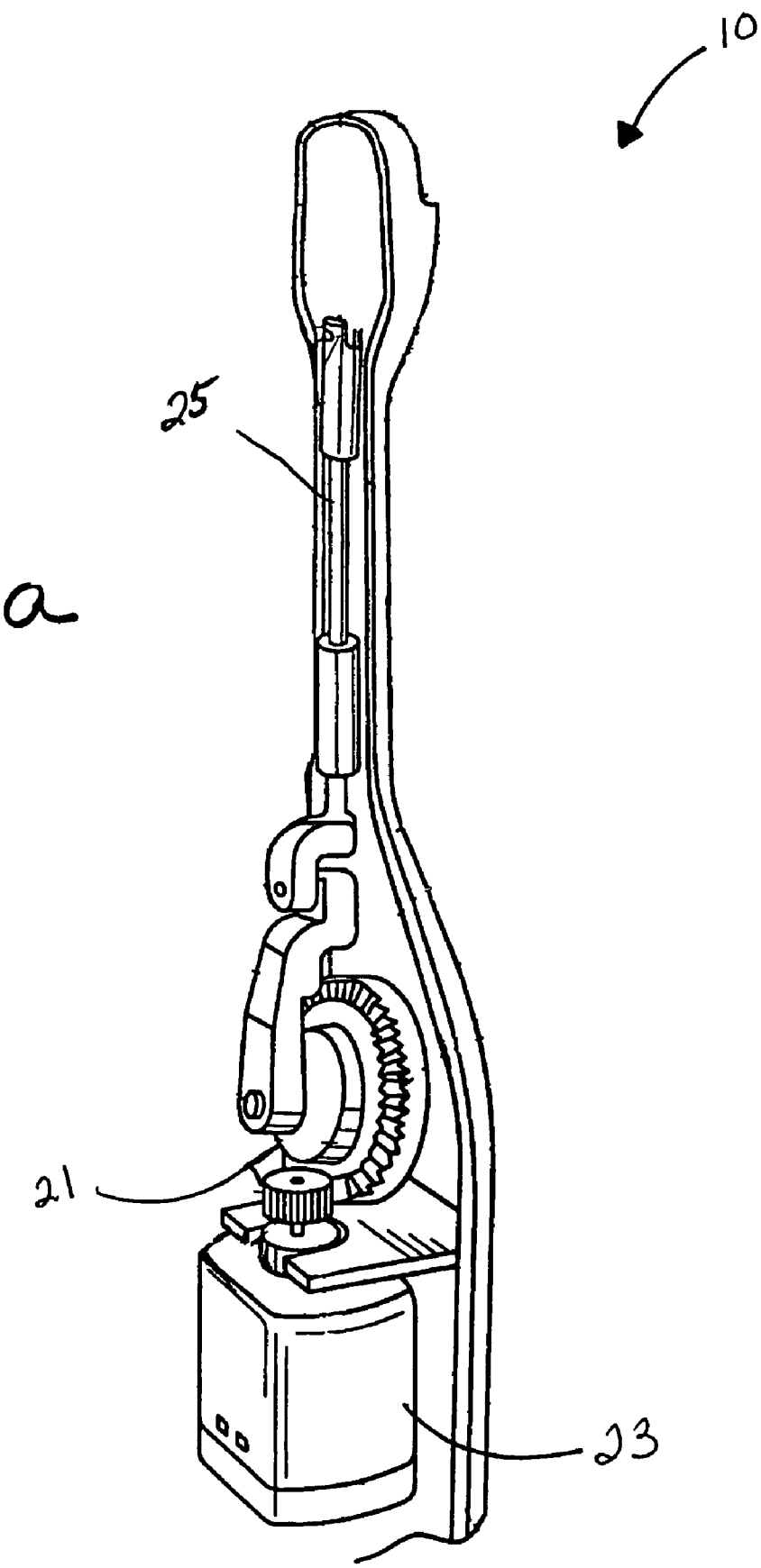
FIG. 1a is a detailed cut away perspective view of an embodiment of the toothbrush in accordance with the present invention.

Referring to FIGS. 1 and 1a, a preferred embodiment toothbrush 10 according to the present invention is illustrated. The toothbrush 10 comprises a body or housing having a handle 30, a head 20 and a neck 40 extending between the handle 30 and the head 20. The head 20 defines a distal-most end 22. The head 20 and the neck 40 generally extend along a longitudinal axis illustrated in FIG. 1 as axis L. Disposed along the head 20 are a plurality of fixed bristles 60, a plurality of intermittently movable bristles 70, and a collection of interiorly disposed bristles 50 which are movable as described herein. The bristles 50 are supported on and retained by a movable bristle holder (not shown in FIG. 1). The movable bristle holder may undergo a wide variety of motions as noted herein as a result of an operative connection with the drive shaft 25. The toothbrush 10 further comprises a motor 23, batteries or other power source (not shown), and a drive mechanism 21 all preferably disposed within a hollow interior region defined within the body or housing and specifically, within the handle 30 and neck 40. One or more switches 35 are provided to selectively operate the motor and drive mechanism.

Figure 2:
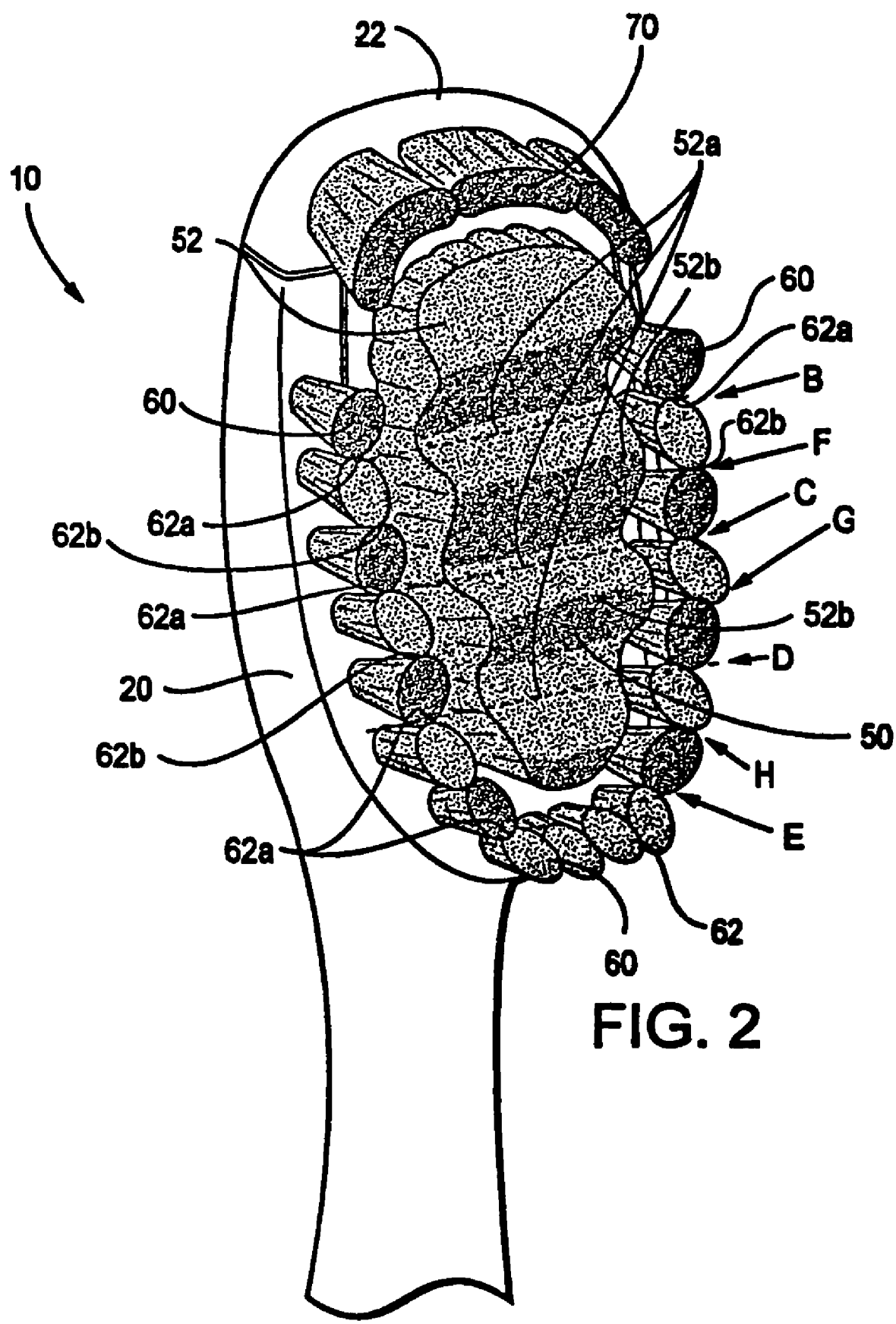
FIG. 2 is a detailed perspective view of the head portion of the electric toothbrush shown in FIG. 1.

FIGS. 2-6 illustrate various preferred embodiment configurations for the arrangement of the fixed bristles, the intermittently movable bristles, and the movable bristles. FIG. 2 is a detailed view of the toothbrush 10 shown in FIG. 1 and its head 20. As can be seen from FIG. 2, the fixed bristles 60 generally extend entirely around a majority of the collection of movable bristles 50. The movable bristles 50 are disposed and situated on a movable bristle holder (not shown). The bristle holder is preferably movable between two positions. Preferably, the bristle holder may be moved back and forth between a first position, in which the bristle holder is proximate the distal-most end 22 of the brush head 20, and a second position in which the bristle holder is at its maximum distance from the distal end 22 of the head 20. Most preferably, the direction of movement of the bristle holder as it reciprocates between these two positions is generally parallel to the longitudinal axis of the head 20 and neck (not shown in FIG. 2) as noted in FIG. 1 as axis L. Disposed adjacent the distal end 22 of the head 20 is a plurality of intermittently movable bristles 70. As will be appreciated, the intermittently movable bristles 70 are located on the brush head 20 such that during reciprocation of the bristle holder and the movable bristles 50, at least a portion of the intermittently movable bristles 70 are periodically contacted by the holder, and optionally by a portion of the movable bristles 50, thereby causing periodic displacement of the bristles 70.

Figure 3:
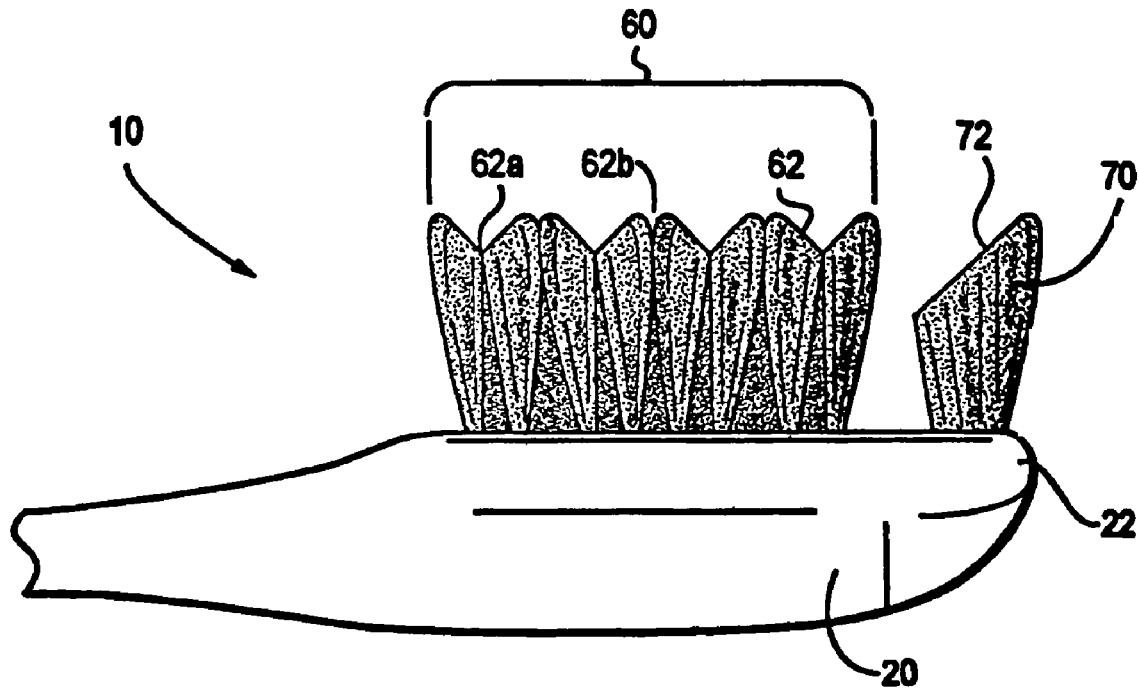
FIG. 3 is a detailed side elevational view of the toothbrush head shown in FIG. 2 having a portion of the bristles removed for clarity.

FIG. 3 is a side elevational view of the head portion 20 of the preferred embodiment toothbrush 10 shown in FIGS. 1 and 2. FIG. 3 illustrates the head portion 20 having the interior collection of movable bristles 50 removed. FIG. 3 illustrates a particularly preferred bristle tip configuration for the group of fixed bristles 60 and the intermittently movable bristles 70. In this preferred aspect, the ends or tips of the plurality of fixed bristles 60 form a serrated brushing surface 62. Specifically, referring to FIG. 3, it can be seen that the serrated brushing surface 62 is characterized by a plurality of valleys or depressions 62a and a plurality of peaks 62b. Similarly, the intermittently movable bristles also define a brushing surface 72. Preferably, the brushing surface 72 extends along an acute angle relative to the longitudinal axis of the toothbrush 10. This preferred aspect for the brushing surface 72 is referred to herein as an inclined brushing surface.

Figure 4:
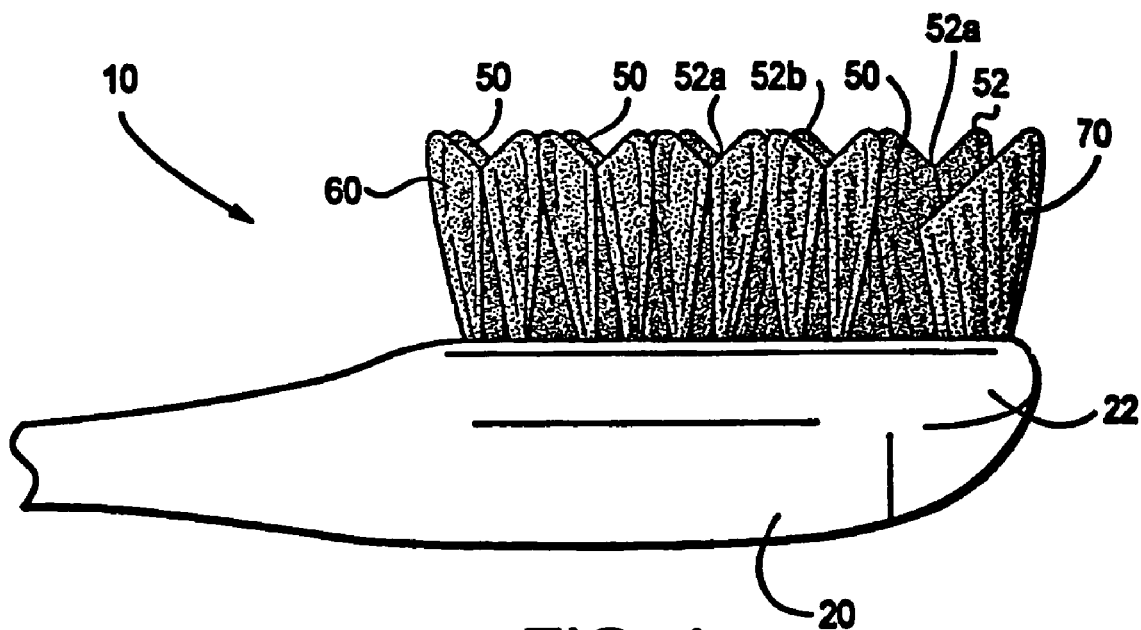
FIG. 4 is a detailed side elevational view of the head portion of the electric toothbrush shown in FIG. 2 with all bristles present.

FIG. 4 illustrates a similar side elevational view of the head portion 20 of the preferred embodiment toothbrush 10. FIG. 4, however, depicts the toothbrush head as also including the movable bristles 50 not depicted in FIG. 3. As best shown in FIGS. 2 and 4, it is preferred in this embodiment, that the brushing surface 52 provided by the interior group of movable bristles 50 is similar to that of the stationary bristles 60. The brushing surface 52 includes a plurality of valleys or depressions 52a and a plurality of peaks 52b. As previously described with respect to the brushing surface 62 of the fixed bristles 60, it is preferred that the brushing surface 52 of the movable bristles 60 is serrated. Specifically, the spacing between the various peaks and valleys of bristle heights or tips for the stationary bristles 60 essentially corresponds to that of the interior group of movable bristles 50. This feature is best depicted in FIG. 2 in which at a certain position of the bristle holder and movable bristles 50 along the head 20, the various peaks and valleys defined by the serrated brushing surface 52 of the movable bristles 50 and the peaks and valleys defined by the serrated brushing surface 62 of the fixed bristles 60 are aligned with one another. Referring to FIG. 2, it can be seen that the depressions 52a of the brushing surface 52 are generally aligned with the depressions 62a of the brushing surface 62 along lines B, C, D and E. And, with further reference to FIG. 2, it can be seen that the peaks 52b of the brushing surface 52 are generally aligned with the peaks 62b of the brushing surface 62 along lines F, G, and H.

Figure 5:
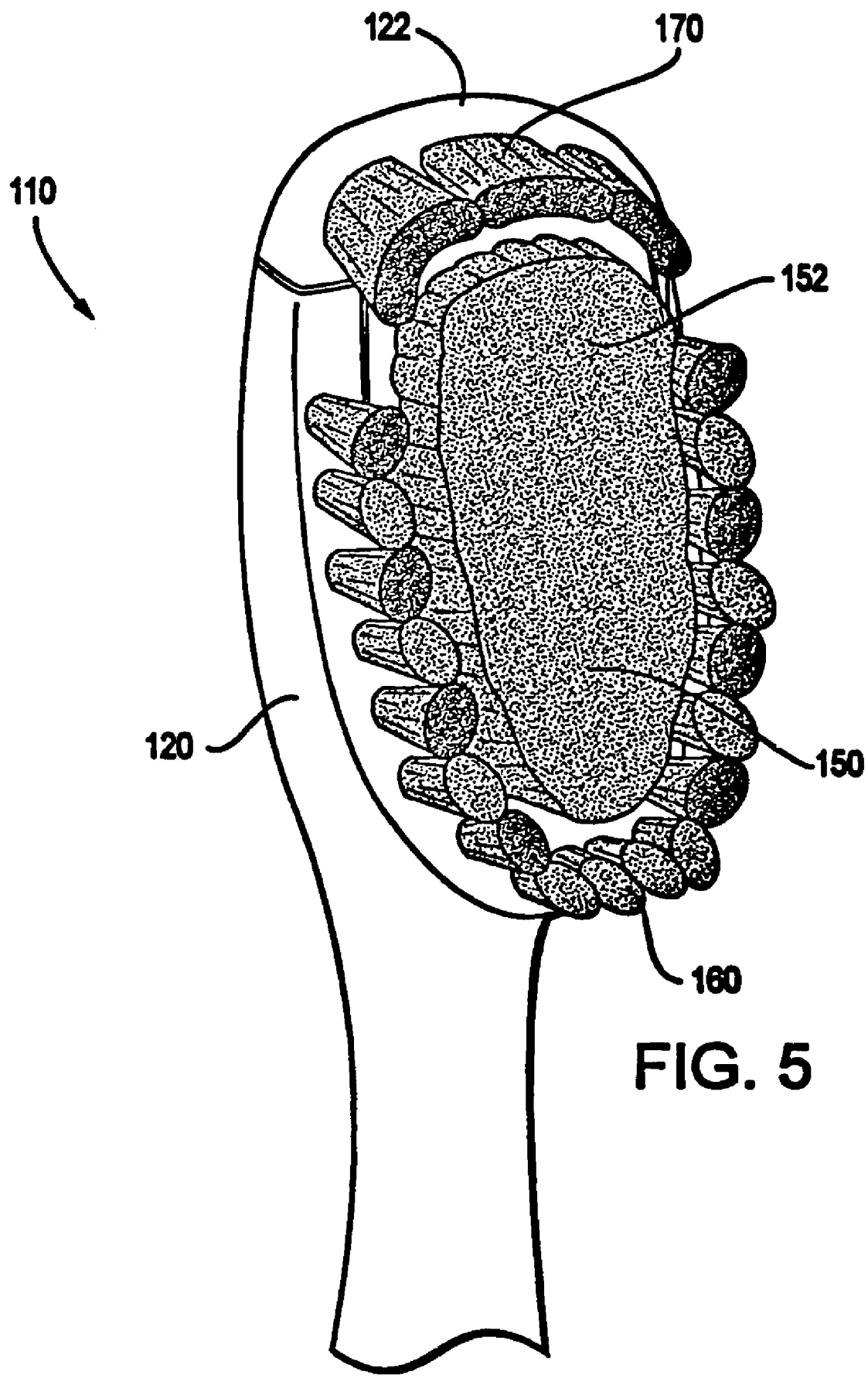
FIG. 5 is a detailed perspective view of a head portion of a second preferred embodiment toothbrush in accordance with the present invention.

FIG. 5 is a detailed perspective view of a head portion of a second preferred embodiment toothbrush in accordance with the present invention. The toothbrush 110 includes a plurality of stationary and/or fixed bristles 160 generally encircling or partially encircling, an interiorly disposed group of movable bristles 150. Disposed on the distal end 122 of the brush head 120 are a plurality of intermittently movable bristles 170. The preferred embodiment toothbrush 110 generally corresponds to the previously described toothbrush 10 shown in the previously noted figures. However, the bristle tip configuration, i.e. brushing surface 152, of the movable bristles 150 differs from the brushing surface 52 of the movable bristles 50 shown in FIG. 2. Essentially, the embodiment depicted in FIG. 5 utilizes a bristle configuration for the movable bristles 150 in which the bristles 150 have a similar or uniform height. This results in a relatively flat or planar brushing surface 152. It is preferred that the intermittently movable bristles 170 define an inclined brushing surface. And, it is preferred that the stationary bristles 160 define a serrated brushing surface.

Figure 6:
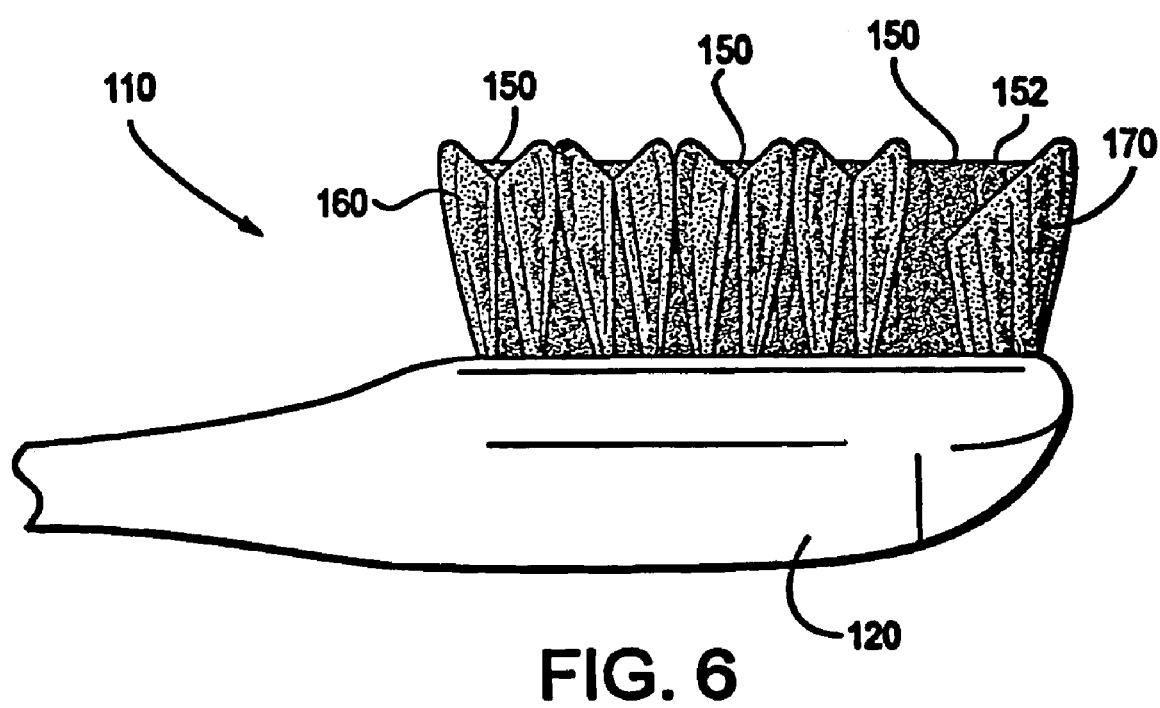
FIG. 6 is a detailed side elevational view of the head portion of the toothbrush shown in FIG. 5.
Figure 7:
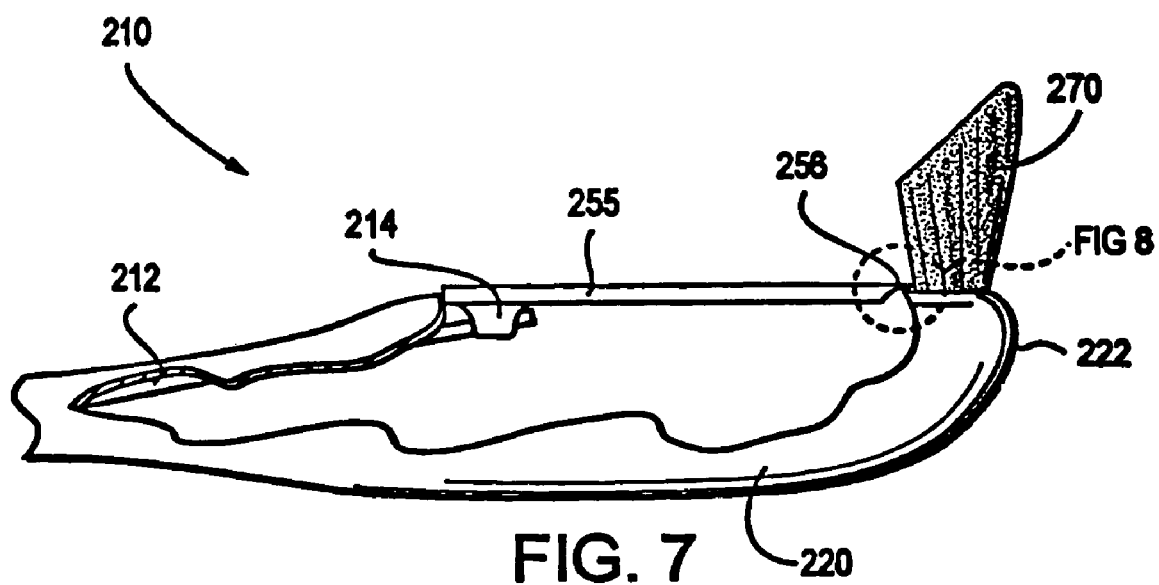
FIG. 7 is a detailed schematic partial sectional view of a head portion of another preferred embodiment toothbrush in accordance with the present invention.

FIG. 6 illustrates this preferred configuration. Specifically, FIG. 6 illustrates a side elevational view of the brush head 120 of the preferred embodiment toothbrush 110. The relatively flat brushing surface 152 of the movable bristles 150 can be seen.

Figure 8:
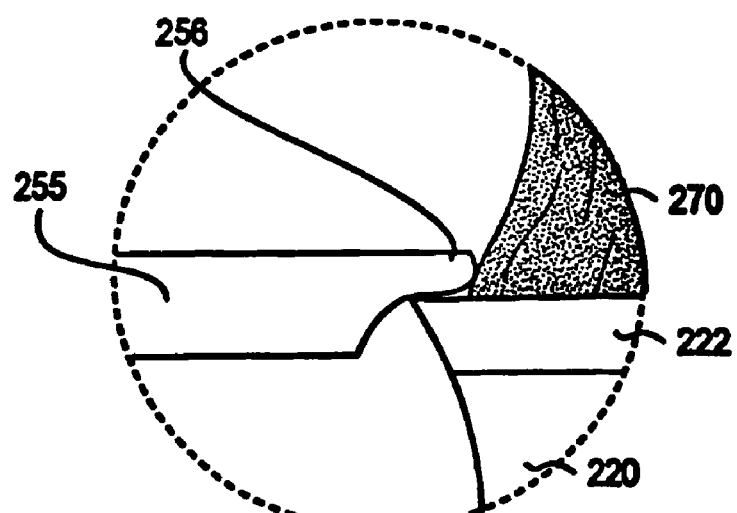
FIG. 8 is a detailed view of a region of the head portion of the preferred embodiment toothbrush shown in FIG. 7.
Figure 9:
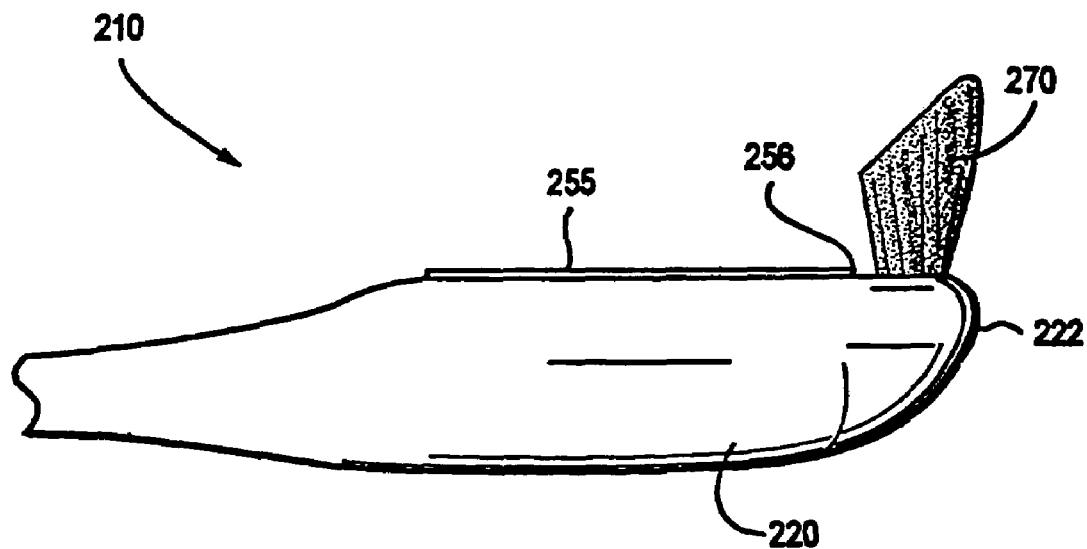
FIG. 9 is a detailed side elevational view of the head portion of the preferred embodiment toothbrush shown in FIG. 7.
Figure 10:
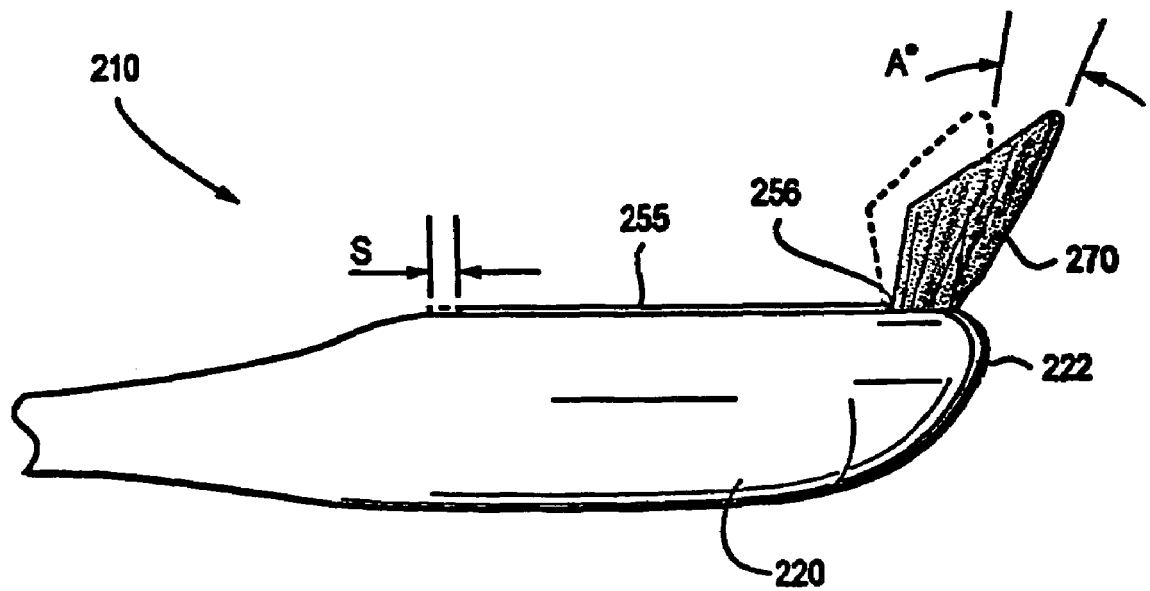
FIG. 10 is another detailed side elevational view of the head portion of the preferred embodiment toothbrush shown in FIG. 7, illustrating displacement of a group of bristles during operation of the toothbrush.

FIGS. 7 to 10 illustrate another preferred embodiment toothbrush 210 in accordance with the present invention. Toothbrush 210 includes a brush head 220 having a plurality of stationary and/or fixed bristles (not shown), movable bristles comprising bristles (not shown) disposed on a movable bristle holder 255, and a plurality of intermittently movable bristles 270 disposed at a distal end 222 of the brush head 220. The bristle holder 255 is engaged to a reciprocating drive shaft 212 by a coupling 214. The drive shaft 212 extends within a hollow region defined in the neck and head of the toothbrush 210 and engages the holder 255 to a motor and drive mechanism (not shown). As will be understood by those skilled in the art, the holder 255 may include support means for assisting or guiding the movement of the holder in relation to the brush head 220. Disposed or defined along the distal end of the holder 255 is an extension region 256. This region is also referred to herein as the contacting edge of the bristle holder. This contacting edge may be located on any area of the bristle holder including, but not limited to, the sides, front/leading edge, and/or the back/trailing edge or any combination thereof. This contacting edge may also comprise protuberances. Protuberances are bulges or projections that extend from the contacting edge of the movable bristle holder to contact the intermittently movable bristles. The contacting edge may comprise one or more protuberances. If a plurality of protuberances are present, spaces or voids may exist between the protuberances. If these spaces and/or voids are present the bristles that correspond to these spaces and/or voids are not moved by the movable bristle holder, therefore, these bristles can be static fixed bristles. In the embodiment having a plurality of protuberances the static fixed bristles can be located next to intermittently movable bristles. The pattern of static fixed bristles and intermittently movable bristles can be determined by the characteristics of the protuberances, including, but not limited to, the number, size, and location of the protuberances. FIG. 8 illustrates a front/leading edge contacting the intermittently movable bristles. The length dimension of the edge 256 is such that upon a forward extension of the bristle holder 255, i.e. towards the distal end 222 of the brush head 220, the intermittently movable bristles 270 are contacted and displaced at some angle. Thus, upon movement of the holder 255, the intermittently movable bristles 270 are displaced at a corresponding frequency as that of the holder 255 during operation of the toothbrush. The extent of displacement of the intermittently movable bristles 270 is shown in FIG. 10 and designated as angle A. It will be appreciated that upon movement of the holder 255, such as defined by stroke length S, the intermittently movable bristles 270 will be displaced at some angle A. The stroke length S for the reciprocating bristle holder of the preferred embodiment toothbrushes described herein may range from about 0.1 mm or less to about 10 mm, more preferably from about 0.5 mm to about 5 mm, and most preferably from about 1 mm to about 3 mm. The angle of displacement A of the intermittently movable bristles, of the preferred embodiment toothbrush as described herein, may range from about 5 degrees to about 45 degrees, more preferably from about 10 degrees to about 35 degrees, and most preferably from about 15 degrees to about 30 degrees. This angle of displacement A, is generally the angular displacement of the bristles of the group of intermittently movable bristles that are located closest to the distal end of the brush head. The angle A is taken as the difference between the orientation of these bristles prior to displacement, shown by the dashed line in FIG. 10, and the orientation of the bristles upon maximum displacement.

As will be understood, in a preferred aspect of the present invention, the bristle holder and particularly, a leading edge of the holder, contacts or impacts intermittently movable bristles upon operation (or initiation of a desired brushing mode) of the toothbrush. Generally, the location of the contact or impact between the bristle holder and an intermittently movable bristle undergoing contact with the holder, may be expressed as a percentage of the total height of the bristle as measured from the face or exposed surface of the brush head from which the intermittently movable bristle extends, to the distal end of the intermittently movable bristle. Generally, the location of contact occurs within a region defined along the lower 50% of the bristle length, preferably along the lower 40%, more preferably along the lower 30%, more preferably along the lower 20%, and most preferably along the lower 10%. Additionally, the contact can be with the base or bulb of the bristle.

Figure 13:
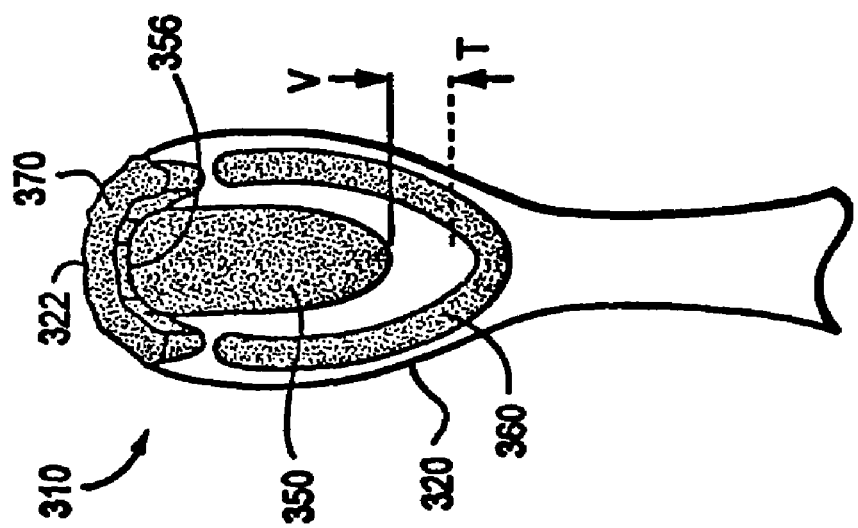
FIG. 13 is yet another view of the head portion of the toothbrush shown in FIG. 11 illustrating further movement of the bristle holder along the head portion.
Figure 12:
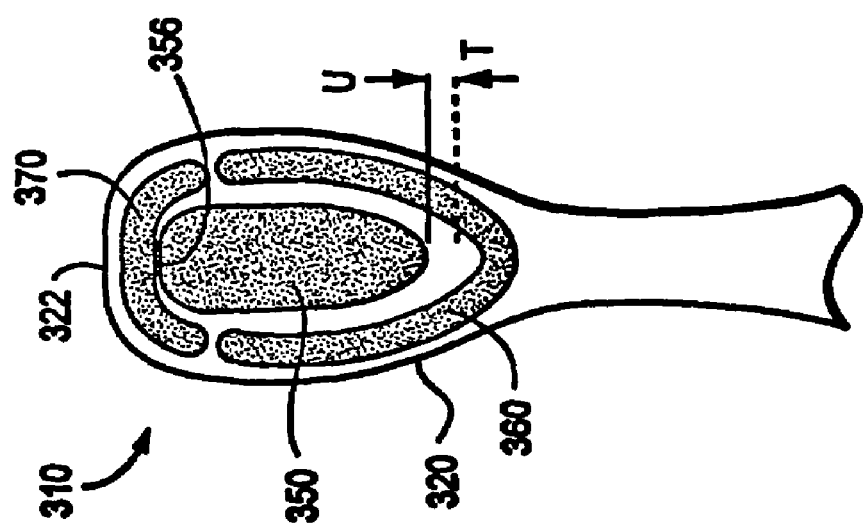
FIG. 12 is another detailed view of the head portion of the toothbrush shown in FIG. 11 illustrating movement of a bristle holder along the head portion.
Figure 11:
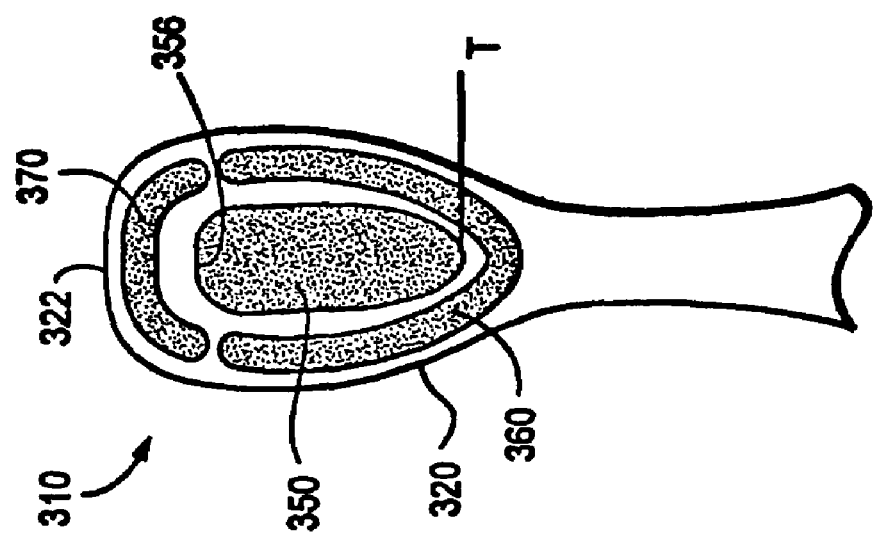
FIG. 11 is a detailed view of the front face of the head portion of another preferred embodiment toothbrush in accordance with the present invention.

FIGS. 11 to 13 illustrate, in yet another fashion, the relationship between movement of the bristle holder and the intermittently movable bristles. Specifically, these figures illustrate a preferred embodiment toothbrush 310 having a head 320. Disposed on the head 320 is a plurality of stationary bristles 360 that generally encircle or partially surround a plurality of moveable bristles 350. The movable bristles 350 are disposed on a movable bristle holder (not shown). Disposed along a distal end 322 of the head 320 is a plurality of intermittently movable bristles 370. During operation of the toothbrush 310 and reciprocation of the bristle holder in a direction generally parallel with the longitudinal axis of the toothbrush 310, the holder reaches a location at which it is at its maximum distance from the end 322 of the brush head 320. This position is shown in FIG. 11 as location T. As the bristle holder begins its stroke toward the end 322 of the brush head 320, the holder reaches a location at which its leading edge 356 contacts at least a portion of the intermittently movable bristles 370. This location occurs at a distance from location T shown in FIG. 12 as distance U. Preferably, distance U, expressed as a percentage of the maximum stroke length of the holder is from about 90% to about 98%. Upon reaching the end of its stroke, i.e. the location of the holder at which its edge 356 is closest to the distal end 322 of the head, the edge 356 contacts at least a portion of the intermittently movable bristles 370 thereby displacing those bristles to their maximum angular displacement. At this location, the distance V, shown in FIG. 13, corresponds to the stroke length of the bristle holder. Generally, the stroke length for a reciprocating bristle holder as described herein, corresponds to the previously described values for S shown in FIG. 10. And, the amount of angular displacement for the intermittently movable bristles 370 corresponds to the previously described values for A shown in FIG. 10.

Figure 16:
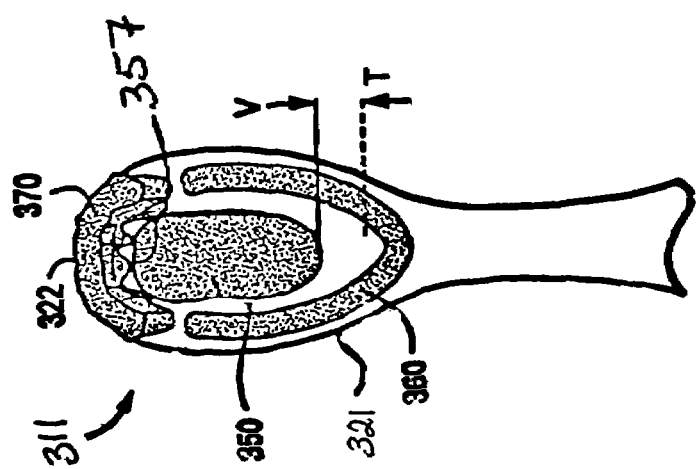
FIG. 16 is yet another view of the head portion of the toothbrush shown in FIG. 14 illustrating further movement of the bristle holder along the head portion.
Figure 15:
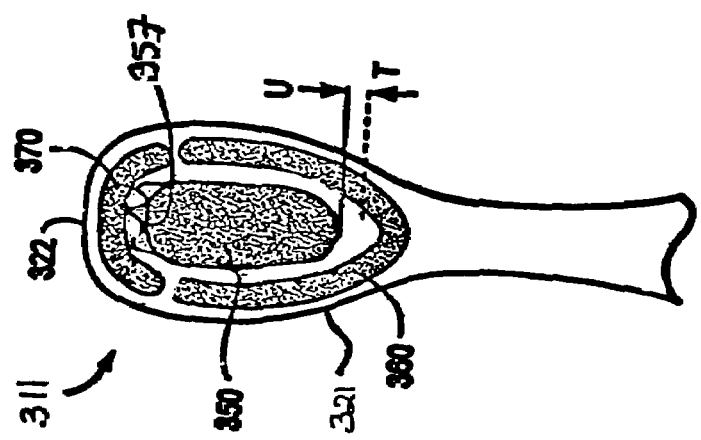
FIG. 15 is another detailed view of the head portion of the toothbrush shown in FIG. 14 illustrating movement of a bristle holder along the head portion.
Figure 14:
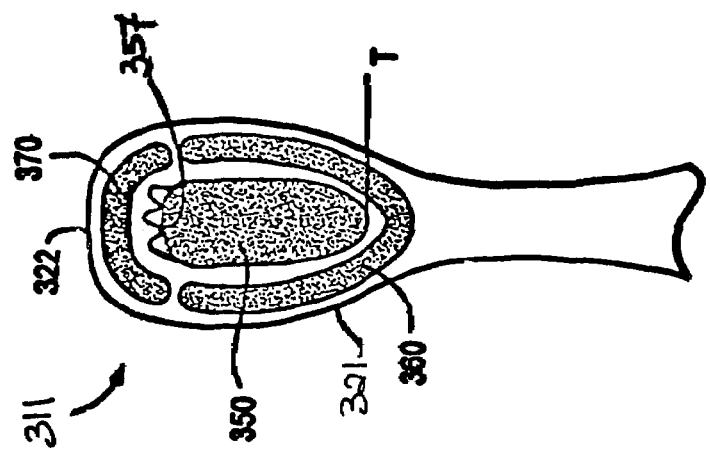
FIG. 14 is a detailed view of the head portion of another preferred embodiment of the toothbrush in accordance with the present invention.

FIGS. 14 to 16 illustrate another embodiment of the invention. These figures illustrate the relationship of a movable bristle holder and the intermittently movable bristles wherein the leading edge of the movable bristle holder comprises protuberances. These protuberances contact the intermittently movable bristles located on the distal end of the toothbrush. The protuberances can be varied in size depending on the type and quantity of movement desired for the intermittently movable bristles. Having larger protuberances can result in a greater amount of movement of the intermittently movable bristles over a greater distance. Also, the protuberances can be formed such that the protuberances impact the intermittently movable bristles from varying angles or contact the bristles at various positions thus creating different types of bristle movement. Disposed on the head 321 is a plurality of stationary bristles 360 that generally encircle or partially surround a plurality of movable bristles 350. The movable bristles 350 are disposed on a movable bristle holder (not shown). In this embodiment of the invention intermittently movable bristles 370 are located on the distal end 322 of the head 321 of the toothbrush 311. During operation of the toothbrush 311 and reciprocation of the bristle holder in a direction generally parallel with the longitudinal axis of the toothbrush 311, the holder reaches a location at which it is at its maximum distance from the distal end 322 of the brush head 321. This position is shown in FIG. 14 as location T. As the bristle holder begins its stroke toward the distal end 322 of the brush head 321, the holder reaches a location at which its leading edge 356 contacts at least a portion of the intermittently movable bristles 370. This location occurs at a distance from location T shown in FIG. 15 as distance U. Preferably, distance U, expressed as a percentage of the maximum stroke length of the holder is from about 90% to about 98%. Upon reaching the end of its stroke, i.e. the location of the holder at which its edge comprising protuberances 357 is closest to the distal end 322 of the head, the protuberances 357 contact at least a portion of the intermittently movable bristles 370 thereby displacing those bristles to their maximum angular displacement. At this location, the distance V, shown in FIG. 16, corresponds to the stroke length of the bristle holder. Generally, the stroke length for a reciprocating bristle holder as described herein, corresponds to the previously described values for S shown in FIG. 10. And, the amount of angular displacement for the intermittently movable bristles 370 corresponds to the previously described values for A shown in FIG. 10.

Figure 19:
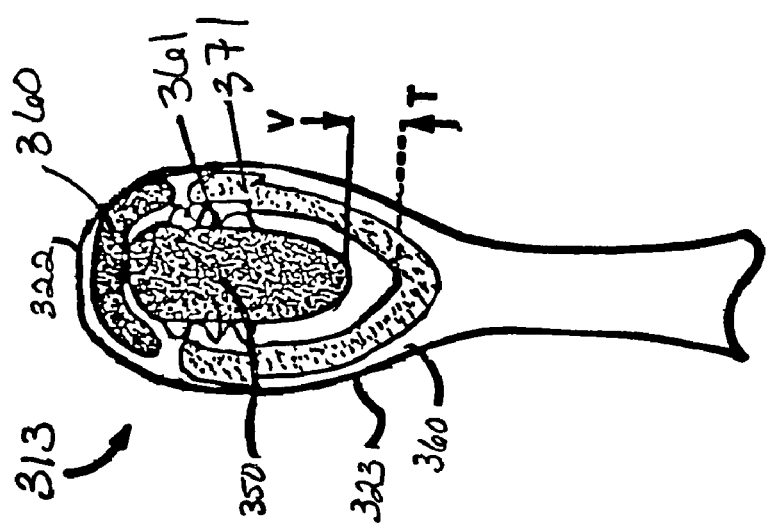
FIG. 19 is yet another view of the head portion of the toothbrush shown in FIG. 17 illustrating further movement of the bristle holder along the head portion.
Figure 18:
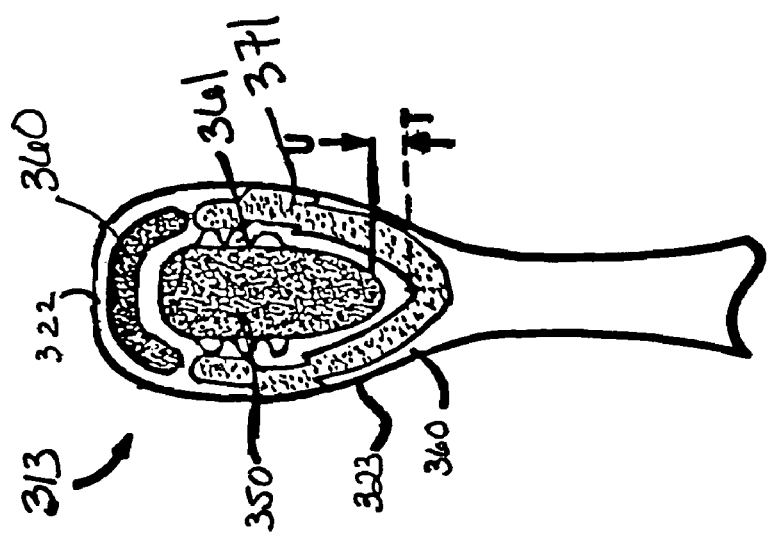
FIG. 18 is another detailed view of the head portion of the toothbrush shown in FIG. 17 illustrating movement of a bristle holder along the head portion.
Figure 17:
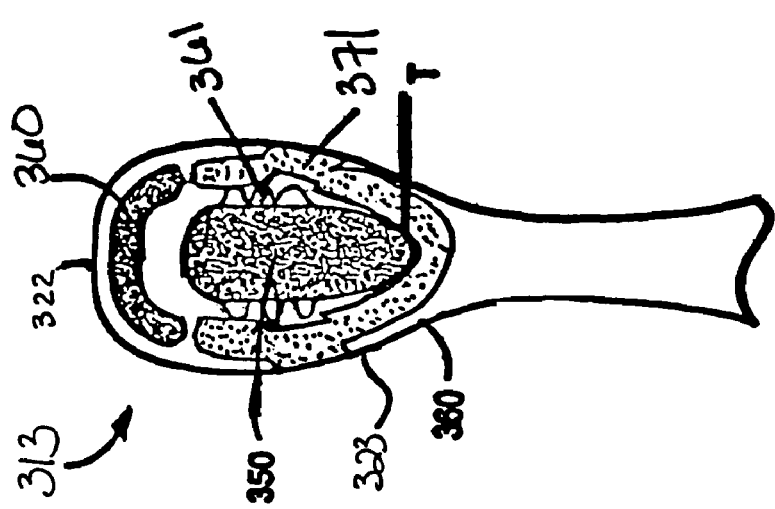
FIG. 17 is a detailed view of the head portion of another preferred embodiment of the toothbrush in accordance with the present invention.

FIGS. 17 to 19 illustrate yet another embodiment of the present invention. Disposed on the head 323 is a plurality of stationary bristles 360 that generally encircle or partially surround a plurality of movable bristles 350. The movable bristles 350 are disposed on a movable bristle holder (not shown). In this embodiment of the invention the intermittently movable bristles 371 are located on the sides of the bristle bearing surface of the head 323 of the toothbrush 313. During operation of the toothbrush 313 and reciprocation of the bristle holder in a direction generally parallel with the longitudinal axis of the toothbrush 313, the bristle holder reaches a location at which it is at its maximum distance from the distal end 322 of the brush head 323. As the bristle holder moves along its stroke toward the distal end 322 of the brush head 323, the holder comprising protuberances 361, located on the sides of the movable bristle holder, contact the intermittently movable bristles 371, disposed along the sides of the head 323 of the toothbrush 313, displacing the bristles as the movable bristle holder moves toward the distal end 322 of the head of the toothbrush 313.

Figure 22:
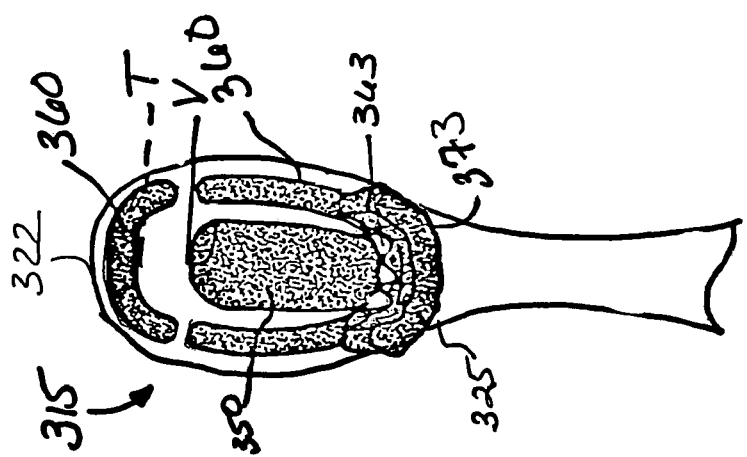
FIG. 22 is yet another view of the head portion of the toothbrush shown in FIG. 20 illustrating further movement of the bristle holder along the head portion.
Figure 21:
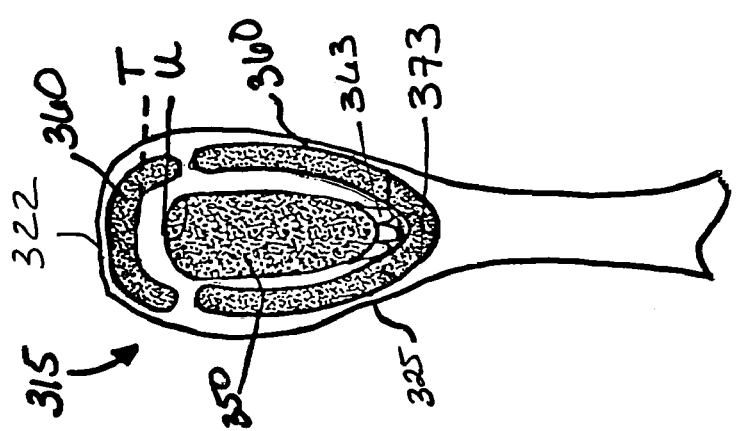
FIG. 21 is another detailed view of the head portion of the toothbrush shown in FIG. 20 illustrating movement of a bristle holder along the head portion.
Figure 20:
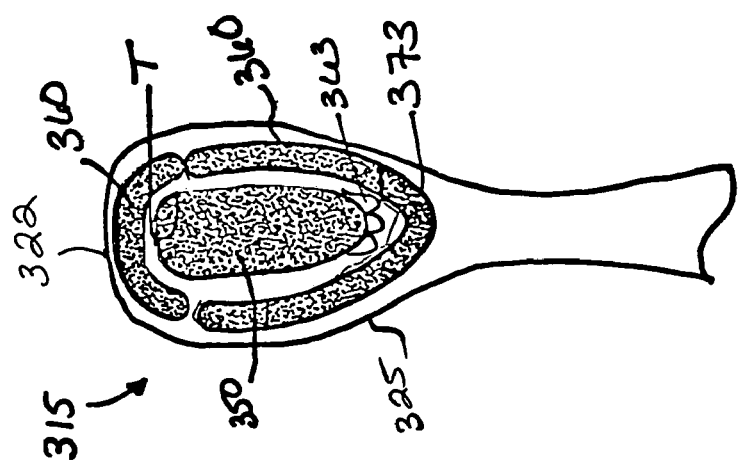
FIG. 20 is a detailed view of the head portion of another preferred embodiment of the toothbrush in accordance with the present invention.

FIGS. 20 to 22 illustrate another embodiment of the present inventive toothbrush. Disposed on the head 325 is a plurality of stationary bristles 360 that generally encircle or partially surround a plurality of movable bristles 350. The movable bristles 350 are disposed on a movable bristle holder (not shown in FIGS. 20 to 22). In this embodiment the intermittently movable bristles 373 are located on portion of toothbrush head 325 proximal to the neck of toothbrush 315. During operation of the toothbrush 315 and reciprocation of the bristle holder in a direction generally parallel with the longitudinal axis of the toothbrush 315. As the bristle holder moves along its stroke from the distal end 322 toward the bottom or proximal end of the toothbrush head 325 the holder comprising protuberances 363, located on the bottom/trailing edge of the movable bristle holder, contact the intermittently movable bristles 373 disposed along the bottom or proximal end of the toothbrush head 325. Upon contact with the protuberances the intermittently movable bristles 373 are displaced.

FIGS. 23 to 24 illustrate another embodiment of the present inventive toothbrush. Intermittently movable bristle(s) 390 is disposed through the static portion 391 of the toothbrush head. The movable bristle holder 397 comprises protuberances 393 that extend underneath the static portion of the head and contact the bulb and/or base 395 of the intermittently movable bristle(s). As the bristle holder begins its stroke toward the distal end 399 of the brush head, the holder reaches a location at which its leading edge 393 contacts the base and/or bulb 395 of the intermittently movable bristle(s) 390. When the leading edge 393 contacts the base and/or bulb 395 the bristle 390 is moved in an upward motion. Then the movable bristle holder 397 completes its stroke cycle by moving back away from the distal end 399 of the toothbrush head, and the edge 393 of the bristle holder 397 moves from away from the base and/or bulb 395 of the intermittently movable bristle 390 resulting in the bristle moving in a downward motion.

In other embodiments of the invention the intermittently movable bristles are disposed on a flexible platform and/or plate. This platform is disposed on or supported by the head of the toothbrush. When the movable bristle contacts either the intermittently movable bristles and/or the flexible platform all the bristles disposed within the platform will intermittently move. Additionally, the platform can contact other bristles, thus imparting motion to these bristles.

In brush head configurations utilizing a reciprocating bristle holder, it is generally preferred that the frequency of the holder is from about 250 to about 5,000 stroke cycles per minute. More preferably, the frequency is in the range of from about 750 to about 2,000 stroke cycles per minute, and typically in the vicinity of about 1,250 stroke cycles per minute. These operating speeds are given with respect to no brushing load being placed upon the bristle holder. It is contemplated that the present invention may employ drive components or bristle holders that contact the intermittently movable bristles which undergo movement at frequencies less than or greater than those noted herein. Additionally, frequency ranges can be affected by dampening the movement of the movable bristle holder.

For brush head configurations utilizing a reciprocating bristle holder that periodically contacts intermittently movable bristles, a particular head design has been found to provide an attractive combination of performance and manufacturability characteristics. In this aspect of the invention, the brush head includes a bristle holder that reciprocates along an axis generally parallel to the longitudinal axis of the toothbrush. The bristle holder defines a leading edge that periodically contacts a set of intermittently movable bristles disposed along or near the distal end of the brush head. The leading edge extends outward from the forward-most region of the base of the holder, a distance of from about 0.1 mm to about 5 mm, more preferably about 0.5 mm to about 4 mm, and most preferably about 2 mm. Referring to FIG. 8, this distance is the distance as measured (along the length dimension of the bristle holder) from the forward-most region of the planar underside of the holder 255 to the distal end of the edge 256 shown in that figure as contacting the intermittently movable bristles 270. The stroke length of the bristle holder under discussion may be as previously described, but is preferably from about 1.0 mm to about 2.5 mm, more preferably from about 1.5 mm to about 2.0 mm, and most preferably about 1.7 mm. The leading edge may also be shaped to have protrusions which impact the intermittently movable bristles and/or bristles.

It will be noted that the preferred bristle configurations are based upon the movable bristles located generally within a middle region or interior of the brush head, and stationary or fixed, and/or intermittently movable bristles at least partially surrounding the medially disposed movable bristles. This is explained in greater detail herein. However, the present invention is not limited to these preferred configurations.

For certain applications, it is preferred that the combination of the stationary or fixed bristles and the intermittently movable bristles surround 100% of the perimeter or periphery of the collection of movable bristles. In other applications, it is preferred that the combination of fixed bristles and intermittently movable bristles surround or extend along about 75% to about 100% of the perimeter of the movable bristles. In still other applications, it is preferred that the combination of fixed bristles and intermittently movable bristles extend along about 50% to about 75% of the perimeter of the movable bristles. In further applications, it is preferred that the combination of fixed bristles and intermittently movable bristles extend along about 25% to about 50% of the perimeter of the movable bristles. And in other applications, it may be preferred that the combination of fixed bristles and intermittently movable bristles extend less than 25% around the perimeter of the movable bristles. As noted, the fixed bristles preferably extend along at least a portion of the outer periphery of the collection of movable bristles. It is not necessary that the fixed bristles extend continuously about the periphery of the set of movable bristles. That is, the present invention encompasses bristle configurations in which the fixed bristles extend partially along or about the outer periphery of the collection of movable bristles.

And, although all preferred embodiment toothbrushes described herein utilize a plurality of intermittently movable bristles disposed near a distal end of the brush head, the present invention includes a wide variety of other arrangements and configurations. For example, a toothbrush in accordance with the present invention could include one, two or more groups or sets of intermittently movable bristles, and provide such groups along various regions of the brush head. That is, the present invention is not limited to the intermittently movable bristles being disposed proximate the distal end. Those bristles could be disposed proximate the neck, or along one or both sides of the head, depending upon the type of motion of the bristle holder. The present invention includes brush head configurations in which the intermittently movable bristles are disposed at nearly any region on the brush head. In one embodiment the perimeter of the head of the toothbrush comprises about 5% to about 25% intermittently movable bristles at the distal end of the head of the toothbrush and the balance of the perimeter of the head of the toothbrush comprises about 95% to about 75% fixed bristles filling the sides and proximal end of the head in a substantially U shape. In another embodiment of the toothbrush the perimeter of the head of the toothbrush substantially comprises intermittently movable bristles. In yet another embodiment the perimeter of the head of the toothbrush comprises about 5% to about 25% of intermittently movable bristles at the distal end of the head of the toothbrush, and about 5% to about 25% of intermittently movable bristles at the proximal end of the head of the toothbrush, and the balance of the perimeter of the head of the toothbrush comprising fixed bristles. In yet another embodiment the perimeter of the head of the toothbrush comprises about 50% to about 75% intermittently movable bristles disposed on the sides of the perimeter of the head of the toothbrush and the balance of the perimeter of the head of the toothbrush comprising fixed bristles.

As noted, the movable bristle holder may undergo a wide variety of motions. For example, the movable bristle holder may undergo angular motion, linear motion, or curvilinear motion. The movement of the bristle holder may be constant or periodic. Alternatively, it is contemplated that the holder may undergo a wide array of motions including such motions best characterized as gyration-like or vibratory. Generally, however, the preferred motion for the movable bristle holder is periodic linear motion or reciprocation.

The various reciprocating bristle holders described herein may also utilize a drive mechanism that provides a shaft that rotates. Furthermore, it will be appreciated that other motor and reciprocating or rotating shaft arrangements can be substituted. For example, U.S. Pat. Nos. 5,226,206; 5,524,312; 5,383,242; 5,465,444; 5,504,959; 5,836,030; 4,845,795; 5,404,608; 5,359,747; and 5,617,601, the substances of which are incorporated herein by reference, disclose other motor and reciprocating shaft arrangements that might be suitable. In addition, the toothbrush might be provided with a replaceable head. A suitable arrangement which can be adapted to the present invention is disclosed in U.S. application Ser. No. 09/850,662, filed May 7, 2001, the substance of which is incorporated herein by reference. Similarly, the drive mechanisms disclosed in U.S. application Ser. No. 10/114,780 filed Apr. 3, 2002; and Ser. No. 10/128,018 filed Apr. 22, 2002, both of which are herein incorporated by reference, are also contemplated for use in conjunction with the present invention.

While brush head embodiments of the present invention have been illustrated for simplicity with tufts of bristles that extend in a direction substantially perpendicular to the longitudinal axis of the head from which they extend, it is contemplated that the bristles might be arranged differently to complement or further enhance the fixed bristles or the intermittently movable bristles, or the motion of the movable bristles or that of the intermittently movable bristles. Some or all of the bristles might extend in a direction which forms an acute angle with a top surface of a bristle holder, and may extend in a forward or rearward direction. In another embodiment, some of the bristles might extend outwardly away from the head, in another direction, again forming an acute angle with respect to the top surface of the bristle holder. In yet another embodiment of the invention, the fixed and/or intermittently movable bristles and/or tufts of bristles located on the leading edge or distal most portion of the toothbrush head form an angle with respect to the longitudinal axis of the toothbrush head from which they extend. The angle formed between the bristles and/or tufts and the head from which they extend can be any size preferred. Massaging bristles or bristles of varying height might also be used, such as described in U.S. Pat. Nos. Des. 330,286, and Des. 434,563, the substances of which are incorporated herein by reference. Other preferred bristle arrangements suitable for use include those arrangements described in whole or part in U.S. Pat. Nos. 6,006,394; 4,081,876; 5,046,213; 5,335,389; 5,392,483; 5,446,940; 4,894,880; and International Publication No. WO99/23910; the substances of which are incorporated herein by reference. Additional aspects of brush heads and bristle characteristics, materials, dimensions, arrangements, and aspects which may be suitable for use with the present invention are noted in one or more of the following U.S. Pat. Nos. 6,574,820; 6,564,416; 6,553,604; 6,453,497; and 6,308,367; the substances of which are incorporated herein by reference. Additionally, any bristles disposed on the head of the toothbrush and/or the bristle holder can be comprised of any material including, but not limited to, Thermoplastic elastomer (TPE), Styrene Ethylene Butadiene Styrene (SEBS), Nylon, Non-elastomeric Materials, and Elastomeric Materials, and/or any combination thereof.

The electric toothbrushes of the present invention can be made with any combination of bristle or massaging tip types, dimensions, combinations, angles and arrangements. Tufts of bristles may alternate in height. In one embodiment there are a plurality of tall tufts and a plurality of shorter tufts. The difference in length between the tall tufts and the shorter tufts is between about 0.5 mm and about 2.5 mm in one embodiment and between about 1 mm and about 2 mm in other embodiments. The tall and short tufts of bristles can be provided with different characteristics. For example, the tall tufts of bristles may be relatively soft for gently cleaning and massaging gums of a user while shorter tufts of bristles may be somewhat firmer for interdental cleaning (or vice versa). This arrangement allows the longer (and typically softer) bristles to be pressed, bent and deflected against the gums of the user before the shorter (and typically firmer) bristles contact the teeth and gums of the user. Therefore, for example, soft bristles can be applied with more force while stiffer (and perhaps less comfortable) bristles are applied with less force.

In a particularly preferred embodiment, the present invention provides a bristle configuration in which the movable bristles, i.e. those supported by and secured to the movable bristle holder, have a total bristle length that is less than the length of the stationary bristles that at least partially encircle or extend alongside the movable bristle holder and bristles secured thereto. A further variation of this preferred bristle configuration features a movable bristle holder that is slightly elevated above the outer surface of the head such that the distal ends of the movable bristles are approximately at the same height as the longer stationary bristles extending from the outer surface of the head. Generally, by utilizing movable bristles that have a relatively short length, the distance or stroke of the movable bristle carrier (when undergoing a reciprocating motion) is less than if longer bristles were used. A shorter stroke generally leads to decreased power requirements. This is beneficial since battery demands are then reduced, which may further promote manufacturability and commercialability of the resulting toothbrush. Moreover, by utilizing relatively short length bristles for the movable bristles, and longer bristles for the stationary bristles, a greater proportion of the brushing load is assumed by the stationary bristles. This generally further reduces power demands on the motor and drive mechanism of the toothbrush.

In one embodiment when the movable bristle holder is not moving, the sinusoid peak of the movable bristles disposed on the movable bristle holder is disposed in the valley between the sinusoid peaks of the fixed and/or intermittently movable bristles substantially surrounding and/or encircling the movable bristle holder. In another embodiment the sinusoid peaks of the movable bristles, when the movable bristle holder is not moving, are disposed such that the sinusoid peaks of the movable bristles and the fixed and/or intermittently movable bristles correspond with each other.

In a particularly preferred aspect, the movable bristle holder used in the present invention toothbrush features a particular bristle receiving configuration. Most preferably, the bristle holder defines a plurality of apertures, each adapted for retaining a tuft of bristles, i.e. the movable bristles. The preferred number of apertures ranges from about 16 to about 25, and most preferably about 22. It will be understood that the number of apertures may be less than or greater than these numbers. Each aperture is preferably round and has a diameter of from about 1.0 mm to about 2.0 mm, and most preferably about 1.60 mm. The apertures are uniformly distributed across the surface of the holder.

Additionally, it may, in some embodiments, be preferable to provide the bristle holder having bristles disposed thereon with an inclined brushing face. That is, upon incorporation and assembly of the bristle holder having bristles disposed thereon in the brush head, the surface of the holder directed toward the distal ends of the bristles, preferably is oriented at an angle with respect to the longitudinal axis of the toothbrush. Preferably, this angle is in the range of from about 10 to about 8°, more preferably from about 2° to about 6°, and most preferably about 4°. The inclination is such that the brushing surface is located at increasingly greater distances from the longitudinal axis of the toothbrush as one moves from the neck of the brush toward the distal end of the brush head.

Although the present invention has been described in terms of a movable bristle holder periodically contacting or striking one or more intermittently movable bristles, the present invention includes configurations in which one or more drive mechanism components besides, or in addition to, a bristle holder, contact or impact the intermittently movable bristles.

The present invention has been described with reference to particular preferred embodiments. Modifications and alterations will occur to others upon reading and understanding this specification. Furthermore, although certain arrangements for the fixed, intermittently movable, and movable bristles have been shown and described, the present invention includes a variety of other configurations. It is intended that all such modifications and alterations are included insofar as they come within the scope of the appended claims or equivalents thereof.

What is claimed is:

1. An electric toothbrush comprising:
   (a) a handle, a head, and a neck extending between said handle and said head, said handle having a hollow interior region, and said electric toothbrush having a longitudinal axis;
   (b) a movable bristle holder disposed on said head, said movable bristle holder having a plurality of movable bristles disposed thereon, said movable bristle holder reciprocates along said longitudinal axis of said toothbrush;
   (c) a motor disposed in said hollow interior region, wherein said motor is operatively connected to said movable bristle holder by a drive shaft; and
   (d) one or more bristles disposed in a static portion of said head, wherein motion of said drive shaft results in motion of said bristles disposed on said static portion of said head.

2. The electric toothbrush of claim 1, wherein said movable bristle holder contacts at least a portion of said one or more bristles disposed on said static portion of said head.

3. The electric toothbrush of claim 1, wherein said movable bristle holder reciprocates from about 750 to about 2000 strokes cycles per minute.

4. The electric toothbrush of claim 1, further comprising at least one bristle disposed in said static portion of said head which does not undergo motion as a result of motion of said drive shaft.

5. The electric toothbrush of claim 4, wherein each of said bristles on said movable bristle holder and on said static portion of said head is comprised of a single elastomeric cylinder.

6. The electric toothbrush of claim 1, wherein said bristles disposed on said static portion of said head are displaced in a direction substantially parallel to said longitudinal axis of the toothbrush.

7. The electric toothbrush of claim 1, wherein said bristles disposed on said static portion of said head are displaced in a direction substantially perpendicular to the longitudinal axis of the toothbrush.

8. The electric toothbrush of claim 1, wherein said bristles disposed on said static portion of said head are displaced at an angle of from about 5 degrees to about 45 degrees as a result of motion of said drive shaft.

9. The electric toothbrush of claim 1, wherein said movable bristle holder has a stroke length of from about 0.1 mm to about 10 mm.

10. The electric toothbrush of claim 1, wherein a lower about 50% of the bristle length is contacted by the movable bristle holder.

11. The electric toothbrush of claim 10, wherein a lower about 30% of the bristle length is contacted by the movable bristle holder.

12. The electric toothbrush of claim 1, wherein at least one of said bristles disposed on said static portion of said head passes through said static portion of said toothbrush with each such bristle terminating in a bristle bulb, wherein said bristle bulb is contacted by said movable bristle holder operatively connected to said drive shaft resulting in motion of the length of the bristle proximal to the static portion of the head of the toothbrush.

13. The electric toothbrush of claim 1, wherein said movable bristle holder further comprises at least one protuberance.

14. The electric toothbrush of claim 1, wherein said movable bristle holder comprises at least one protuberance selected from the group consisting of at least one leading edge protuberance, at least one trailing edge protuberance, at least one side edge protuberance and any combination thereof.

15. The electric toothbrush of claim 13, wherein said at least one protuberance is on a leading edge of said movable bristle holder.

16. An electric toothbrush comprising:
   (a) a handle, a head, and a neck extending between said handle and said head, said handle having a hollow interior region, and said electric toothbrush having a longitudinal axis;
   (b) a movable bristle holder disposed on said head, said movable bristle holder having a plurality of movable bristles disposed thereon, said movable bristle holder reciprocates along said longitudinal axis of said toothbrush;
   (c) a motor disposed in said hollow interior region and operatively connected to said movable bristle holder to move said movable bristle holder; and
   (d) one or more bristles disposed in a static portion of said head, wherein movement of said movable bristle holder results in motion of at least a portion of said one or more bristles disposed on said static portion of said head.

17. The electric toothbrush of claim 16, wherein contact occurs between said movable bristle holder and said at least a portion of said one or more bristles disposed on said static portion of said head.

18. An electric toothbrush comprising:
   (a) a handle, a head, and a neck extending between said handle and said head, said handle having a hollow interior region, and said electric toothbrush having a longitudinal axis;
   (b) a movable bristle holder disposed on said head, said movable bristle holder having a plurality of movable bristles disposed thereon, said movable bristle holder includes one or more protuberances and reciprocates along said longitudinal axis of said toothbrush;

(c) a motor disposed in said hollow interior region and operatively connected to said movable bristle holder to move said movable bristle holders; and (d) one or more bristles disposed in a static portion of said head, wherein movement of said movable bristle holder comprising said one or more protuberances moves at least a portion of said bristles disposed on said static portion of said head.

19. The electric toothbrush of claim 18, wherein said movable bristle holder reciprocates from about 750 to about 2000 strokes cycles per minute.

20. The electric toothbrush of claim 18, wherein said one or more protuberances selected from the group consisting of leading edge protuberances, trailing edge protuberances, side edge protuberances and any combination thereof.

21. The electric toothbrush of claim 18, wherein said one or more protuberances are on a leading edge of said movable bristle holder.

22. The electric toothbrush of claim 18, wherein said movable bristle holder comprises a plurality of protuberances.

23. The electric toothbrush of claim 18, wherein contact occurs between said one or more protuberances and said at least a portion of said one or more bristles disposed on said static portion of said head during movement of said movable bristle holder.

24. The electric toothbrush of claim 23, wherein said one or more protuberances contact said bristles disposed on said static portion of said head within the lower about 50% of the bristle length.

25. The electric toothbrush of claim 18, wherein said bristle passes through said static portion of said toothbrush terminating in a bristle bulb, wherein said bristle bulb is contacted by said movable bristle holder resulting in motion of the proximal length of the bristle.

26. The electric toothbrush of claim 16, wherein said movable bristle holder reciprocates from about 750 to about 2000 strokes cycles per minute.

27. The electric toothbrush of claim 16, wherein each of said bristles on said movable bristle holder and on said static portion of said head is comprised of a single elastomeric cylinder.

28. The electric toothbrush of claim 16, wherein said bristles disposed on said static portion of said head are displaced in a direction substantially parallel to said longitudinal axis of the toothbrush.

29. The electric toothbrush of claim 16, wherein the movement of said movable bristle holder results in the motion of said portion of said bristles disposed on said static portion of said head in a direction substantially perpendicular to the longitudinal axis of the toothbrush.

30. The electric toothbrush of claim 16, wherein the movement of said movable bristle holder results in the motion of said portion of said bristles disposed on said static portion of said head through an angle of from about 5 degrees to about 45 degrees as a result of motion of said drive shaft.

31. The electric toothbrush of claim 16, wherein said movable bristle holder has a stroke length of from about 0.1 mm to about 10 mm.

32. The electric toothbrush of claim 16, wherein a lower about 50% of the bristle length is contacted by the movable bristle holder.

33. The electric toothbrush of claim 32, wherein a lower about 30% of the bristle length is contacted by the movable bristle holder.

34. An electric toothbrush comprising:

(a) a handle, a head, and a neck extending between said handle and said head, said handle having a hollow interior region, and said electric toothbrush having a longitudinal axis;

(b) a movable bristle holder disposed on said head, said movable bristle holder having a plurality of movable bristles disposed thereon;

(c) a motor disposed in said hollow interior region, wherein said motor is operatively connected to said movable bristle holder by a drive shaft; and (d) one or more bristles disposed in a static portion of said head, at least one of said bristles disposed on said static portion of said head pass through said static portion of said toothbrush with each such bristle terminating in a bristle bulb, wherein said bristle bulb is contacted by said movable bristle holder operatively connected to said drive shaft so motion of said drive shaft results in motion of the length of the bristle proximal to the static portion of the head of the toothbrush.

35. The electric toothbrush of claim 34, wherein said movable bristle holder reciprocates from about 750 to about 2000 strokes cycles per minute.

36. The electric toothbrush of claim 34, further comprising at least one bristle disposed in said static portion of said head which does not undergo motion as a result of motion of said drive shaft.

37. The electric toothbrush of claim 34, wherein each of said bristles on said movable bristle holder and on said static portion of said head which does not undergo motion as a result of motion of said drive shaft comprises a single elastomeric cylinder.

38. The electric toothbrush of claim 34, wherein said movable bristle holder has a stroke length of from about 0.1 mm to about 10 mm.

39. An electric toothbrush comprising:

(a) a handle, a head, and a neck extending between said handle and said head, said handle having a hollow interior region, and said electric toothbrush having a longitudinal axis;

(b) a movable bristle holder disposed on said head, said movable bristle holder having a plurality of movable bristles disposed thereon, said movable bristle holder includes a plurality of protuberances;

(c) a motor disposed in said hollow interior region and operatively connected to said movable bristle holder to move said movable bristle holder; and (d) one or more bristles disposed in a static portion of said head, wherein movement of said movable bristle holder comprising said plurality of protuberances moves at least a portion of said bristles disposed on said static portion of said head.

40. The electric toothbrush of claim 39, wherein said movable bristle holder reciprocates from about 750 to about 2000 strokes cycles per minute.

41. The electric toothbrush of claim 39, wherein said plurality of protuberances are selected from the group consisting of leading edge protuberances, trailing edge protuberances, side edge protuberances and any combination thereof.

42. The electric toothbrush of claim 39, wherein said plurality of protuberances are on a leading edge of said movable bristle holder.

43. The electric toothbrush of claim 39, wherein contact occurs between said one or more protuberances and said at least a portion of said one or more bristles disposed on said static portion of said head during movement of said movable bristle holder.

44. The electric toothbrush of claim 43, wherein said one or more protuberances contact said bristles disposed on said static portion of said head within the lower about 50% of the bristle length.

45. The electric toothbrush of claim 39, wherein each of said bristles on said movable bristle holder and said static portion of said head is comprised of a single elastomeric cylinder.

46. The electric toothbrush of claim 39, wherein said bristles disposed on said static portion of said head are displaced in a direction substantially parallel to said longitudinal axis of the toothbrush.

47. The electric toothbrush of claim 39, wherein said bristles disposed on said static portion of said head are displaced in a direction substantially perpendicular to the longitudinal axis of the toothbrush.

48. The electric toothbrush of claim 39, wherein said bristles disposed on said static portion of said head are displaced at an angle of from about 5 degrees to about 45 degrees as a result of motion of said drive shaft.

49. An electric toothbrush comprising:
(a) a handle, a head, and a neck extending between said handle and said head, said handle having a hollow interior region, and said electric toothbrush having a longitudinal axis;
(b) a movable bristle holder disposed on said head, said movable bristle holder having a plurality of movable bristles disposed thereon, said movable bristle holder reciprocates along said longitudinal axis of said toothbrush;
(c) a motor disposed in said hollow interior region and operatively connected to said movable bristle holder to move said movable bristle holder; and
(d) one or more bristles disposed in a static portion of said head, wherein at least a portion of said bristles disposed on said static portion of said head pass through said static portion of said toothbrush with each such bristle terminating in a bristle bulb, wherein said bristle bulb is contacted by said movable bristle holder so motion of said movable bristle holder results in motion of the length of the bristle proximal to the static portion of the head of the toothbrush.

50. The electric toothbrush of claim 49, wherein said movable bristle holder reciprocates along said longitudinal axis of said toothbrush.

51. The electric toothbrush of claim 50, wherein said movable bristle holder reciprocates from about 750 to about 2000 strokes cycles per minute.

52. The electric toothbrush of claim 49, wherein some said bristles disposed on said static portion of said head comprise bristles that are disposed in said static portion of said head and do not undergo motion as a result of motion of said movable bristle holder.

53. The electric toothbrush of claim 49, wherein each of said bristles on said movable bristle holder and on said static portion of said head which does not undergo motion as a result of motion of said movable bristle holder is comprised of a single elastomeric cylinder.

54. The electric toothbrush of claim 49, wherein said movable bristle holder has a stroke length of from about 0.1 mm to about 10 mm.

* * * * *